(12) United States Patent
Foi et al.

(10) Patent No.: US 10,803,553 B2
(45) Date of Patent: Oct. 13, 2020

(54) SYSTEMS AND METHODS FOR IMAGE RESOLUTION ENHANCEMENT

(71) Applicants: FLIR Systems, Inc., Wilsonville, OR (US); Noiseless Imaging Oy Ltd., Tampere (FI)

(72) Inventors: Alessandro Foi, Tampere (FI); Enrique Sanchez-Monge, Tampere (FI)

(73) Assignee: FLIR SYSTEMS, INC., Wilsonville, OR (US)

( * ) Notice: Subject to any disclaimer, the term of this patent is extended or adjusted under 35 U.S.C. 154(b) by 98 days.

(21) Appl. No.: 16/028,269

(22) Filed: Jul. 5, 2018

(65) Prior Publication Data
US 2018/0330473 A1 Nov. 15, 2018

Related U.S. Application Data

(63) Continuation of application No. PCT/US2017/012226, filed on Jan. 4, 2017.
(Continued)

(51) Int. Cl.
*G06T 3/40* (2006.01)
*G06T 7/33* (2017.01)
(Continued)

(52) U.S. Cl.
CPC .......... *G06T 3/4053* (2013.01); *A61B 5/0033* (2013.01); *G06T 7/337* (2017.01); *H04N 1/393* (2013.01); *G06T 2207/10028* (2013.01)

(58) Field of Classification Search
CPC ........ A61B 5/0033; G06T 2207/10028; G06T 3/4053; G06T 7/337; H04N 1/393
See application file for complete search history.

(56) References Cited

U.S. PATENT DOCUMENTS 5,796,879 A * 8/1998 Wong .................... G06T 3/4007
358/451
8,520,970 B2 8/2013 Strandemar
(Continued)

OTHER PUBLICATIONS

Foi et al., "Pointwise Shape-Adaptive DCT for High-Quality Deblocking of Compressed Color Images," IEEE Transactions on Image Processing, May 1, 2007, pp. 1395-1411, vol. 16, No. 5, IEEE Service Center, Piscataway, New Jersey.
(Continued)

*Primary Examiner* — Kenny A Cese
(74) *Attorney, Agent, or Firm* — Haynes and Boone, LLP

(57) ABSTRACT

Various techniques are disclosed for systems and methods to provide image resolution enhancement. For example, a method includes: receiving a reference image (e.g., a visible light image) of a scene comprising image pixels identified by pixel coordinates; receiving a lower-resolution target image (e.g., an infrared image) of the scene; resizing the target image to a larger size; determining an adaptive-shape neighborhood for each pixel coordinate, wherein the adaptive-shape neighborhood extends from the each pixel coordinate such that those reference image pixels that are within the shape-adaptive neighborhood meet a regularity condition; determining, for each adaptive-shape neighborhood, a local estimate based on those target image pixels that are within the adaptive-shape neighborhood; and aggregating the local estimates associated with the adaptive-shape neighborhoods to provide a global estimate that corresponds to the target image with an improved resolution. A system configured to perform such a method is also disclosed.

20 Claims, 13 Drawing Sheets

Related U.S. Application Data

(60) Provisional application No. 62/276,800, filed on Jan. 8, 2016.

(51) Int. Cl.
*A61B 5/00* (2006.01)
*H04N 1/393* (2006.01)

(56) References Cited

U.S. PATENT DOCUMENTS

| | | | | |
|---|---|---|---|---|
| 8,565,547 | B2 | 10/2013 | Strandemar | |
| 8,995,793 | B1* | 3/2015 | Laflen | G06T 7/40 |
| | | | | 382/299 |
| 9,171,361 | B2 | 10/2015 | Strandemar | |
| 2010/0209016 | A1* | 8/2010 | Kimata | G06T 3/4007 |
| | | | | 382/284 |
| 2011/0228120 | A1* | 9/2011 | Inoue | H04N 5/23232 |
| | | | | 348/222.1 |
| 2013/0308877 | A1* | 11/2013 | Tezuka | H04N 1/40068 |
| | | | | 382/300 |
| 2014/0015982 | A9* | 1/2014 | Strandemar | G06T 5/50 |
| | | | | 348/164 |
| 2014/0046172 | A1* | 2/2014 | Kim | A61B 5/7275 |
| | | | | 600/411 |
| 2016/0078599 | A1* | 3/2016 | Furihata | G09G 5/391 |
| | | | | 345/667 |

OTHER PUBLICATIONS

Foi et al., "Shape-Adaptive DCT for Denoising and Image Reconstruction," Proceedings of SPIE-International Society for Optical Engineering, Feb. 2, 2006, pp. 60640N-1-60640N-12, vol. 6064, San Jose.

Foi et al., Spatially Adaptive Local Approximations in Signal and Image Processing: Varying-Scale Polynomials, Anisotropic Adaptation, Shape-Adaptive Transforms, EUSIPCO, Mar. 9, 2007, 95 Pages. Retrieved from the Internet: <http://citeseerx.ist.psu.edu/viewdoc/download?doi=10.1.1.76.3265&rep=rep1&type=pdf>.

Katkovnik et al., "Directional Varying Scale Approximations for Anisotropic Signal Processing," $12^{th}$ European Signal Processing Conference, Apr. 6, 2015, pp. 101-104, IEEE.

\* cited by examiner

SYSTEMS AND METHODS FOR IMAGE RESOLUTION ENHANCEMENT

CROSS-REFERENCE TO RELATED APPLICATIONS

This application is a continuation of International Patent Application No. PCT/US2017/012226 filed Jan. 4, 2017 and entitled "SYSTEMS AND METHODS FOR IMAGE RESOLUTION ENHANCEMENT," which is incorporated herein by reference in its entirety.

International Patent Application No. PCT/US2017/012226 filed Jan. 4, 2017 claims priority to and the benefit of U.S. Provisional Patent Application No. 62/276,800 filed Jan. 8, 2016 and entitled "SYSTEMS AND METHODS FOR IMAGE RESOLUTION ENHANCEMENT," which is hereby incorporated by reference in its entirety.

TECHNICAL FIELD

One or more embodiments of the invention relate generally to imaging processing and more particularly, for example, to enhancement of the resolution of images.

BACKGROUND

Super-resolution techniques have been developed to enhance the resolution of imaging systems or images captured by such systems. However, conventional super-resolution techniques are typically limited to enhancing information already captured in the images, for example, by suppressing noise, anti-aliasing, or extrapolating and interpolating pixel information. As such, conventional super-resolution techniques are inadequate to bring out the true structural details and definition that would be captured in a truly higher resolution version of the images.

Such shortcomings of conventional super-resolution techniques generally make them unsuitable for achieving a desired image resolution and definition where the original image contains insufficient information. For example, native images produced by some imaging sensors and devices, such as infrared (IR) imaging sensors, photonic mixer devices (PMD) or other time-of-flight (ToF) imaging sensors, laser imaging detection and ranging (LIDAR) devices, generally have a low resolution, low definition, and/or low signal-to-noise ratio (SNR) due to the specific modalities or spectra in which these sensors and devices operate. While it would be desirable to obtain a true higher resolution version of the images captured by such imaging sensors and devices, conventional super-resolution techniques may be inadequate.

SUMMARY

Various techniques are disclosed for systems and methods to enhance a resolution, definition, and/or signal-to-noise ratio (SNR) of images to provide sharper, easier-to-interpret, more visually pleasing, and more content-rich images and videos for viewing and for further image processing. For example, in one embodiment, a method includes: receiving a reference image of a scene, the reference image comprising reference image pixels identified by pixel coordinates; receiving a target image of the scene, the target image having a lower resolution than the reference image; resizing the target image to a larger image size, the resized target image comprising target image pixels identified by the pixel coordinates of the corresponding reference image pixels; determining an adaptive-shape neighborhood for each pixel coordinate, wherein the adaptive-shape neighborhood extends from the each pixel coordinate such that those reference image pixels that are within the shape-adaptive neighborhood meet a regularity condition; determining, for each adaptive-shape neighborhood, a local estimate based on those target image pixels that are within the adaptive-shape neighborhood; and aggregating the local estimates associated with the adaptive-shape neighborhoods to provide a global estimate that corresponds to the target image with an improved resolution. The method may also be performed on the reference and the target images that are three-dimensional (3-D) volumetric or point-cloud images to enhance the target 3-D images, according to some embodiments.

The reference image may be a visible light image captured by a visible light imaging sensor, and the target image may be an infrared (IR) image captured by an IR imaging sensor, according to some embodiments. In other embodiments, the reference image may be captured by a computed tomography (CT) scanner or magnetic resonance imaging (MRI) device, and the target image is captured by a positron emission tomography (PET) scanner, single-photon emission computed tomography (SPECT) scanner, ultrasound imaging device.

The adaptive-shape neighborhoods may be determined using various techniques according embodiments of the disclosure. For example, the determining of each adaptive-shape neighborhood may comprise determining line-wise extents for a plurality of directions from each pixel coordinate. Each adaptive-shape neighborhood may then be a polygonal hull of the determined line-wise extents for each pixel coordinate, in some embodiments. The line-wise extent for each direction may be determined at least by selecting, according to a statistical method, a local polynomial approximation (LPA) kernel from a set of LPA kernels with different lengths, the length of the selected LPA kernel being determined as the line-wise extent for the each direction. Each selected LPA kernel may be the lengthiest LPA kernel among the set of LPA kernels that provides an acceptable approximation according to the statistical method when the selected LPA kernel is convolved with those reference image pixels along the corresponding direction and length, and the statistical method for selecting LPA kernels may include an intersection of confidence intervals (ICI) method, according to various embodiments. Each adaptive-shape neighborhood determined according to various embodiments may extend anisotropically in a plurality of directions. For 3-D volumetric or point-cloud images, the determining of each adaptive-shape neighborhood may comprise determining adaptive-size cubes from each pixel coordinate.

The local estimate for each adaptive-shape neighborhood may be determined using various techniques according embodiments of the disclosure. For example, the determining of the local estimate for each adaptive-shape neighborhood may comprise averaging those target image pixels that are within each adaptive-shape neighborhood in some embodiments, or filtering those target image pixels that are within each adaptive-shape neighborhood in some embodiments. The filtering of the target image pixels may, for some embodiments, include: performing a shape-adaptive transform on those target image pixels within each adaptive-shape neighborhood to obtain coefficients corresponding to those target image pixels in the domain of the shape-adaptive transform; and modifying (e.g., shrinking by thresholding) the coefficients in the domain of the shape-adaptive transform. The shape-adaptive transform may include a shape-adaptive discrete cosine transform (SA-DCT) or other appropriate transforms.

The aggregating of the local estimates according to some embodiments may comprise averaging the local pixel estimates according to weights associated with the respective local estimates. The weights may be inversely proportional to the number of pixel coordinates belonging to the corresponding adaptive-shape neighborhoods, or the weights may be based on other statistical or quantitative properties associated with the corresponding adaptive-shape neighborhoods.

The determining of the adaptive-shape neighborhoods, the determining of the local estimates, and the aggregating of the local estimates may be repeated with the global estimate used as a new target image, according to some embodiments. The repeating may, for example, be performed with increased sensitivity for the regularity condition for determining the adaptive-shape neighborhoods, such that at least some of the adaptive-shape neighborhoods become smaller to adapt to finer details captured in the reference image than those prior to the repeating.

The method according to some embodiments may further include comparing the global estimate with the target image and adjusting the global estimate based on the comparing to remove or reduce differences in aggregate pixel values between the global estimate and the target image. The method according to some embodiments may include operations to further enhance the global output that corresponds to the target image with an improved resolution. For example, the method may further include extracting edge information from the reference image, and sharpening the global estimate based on the extracted edge information and/or overlaying the edge information onto the global estimate.

In another embodiment, a system includes: a video interface configured to receive image data or signals; a processor in communication with the video interface and configured to: receive a reference image of a scene, the reference image comprising reference image pixels identified by pixel coordinates; receive a target image of the scene, the target image having a lower resolution than the reference image; resize the target image to a larger image size, the resized target image comprising target image pixels identified by the pixel coordinates of the corresponding reference image pixels; determine an adaptive-shape neighborhood for each pixel coordinate, wherein the adaptive-shape neighborhood extends from the each pixel coordinate such that those reference image pixels that are within the shape-adaptive neighborhood meet a regularity condition; determine, for each adaptive-shape neighborhood, a local estimate based on those target image pixels that are within the adaptive-shape neighborhood; and aggregate the local estimates associated with the adaptive-shape neighborhoods to provide a global estimate that corresponds to the target image with an improved resolution; and a memory in communication with the processor and configured to store the global estimate. The processor may be further configured to perform various operations of the method described above for various embodiments. The processor may be configured to perform various operations of the method on the reference and the target images that are three-dimensional (3-D) volumetric or point-cloud images to enhance the target 3-D images, according to some embodiments.

The system may further include a first imaging sensor in communication with the video interface and configured to capture the reference image and a second imaging sensor in communication with the video interface and configured to capture the target image, according to some embodiments. For example, the first imaging sensor may include a visible light (VL) imaging sensor, a ultraviolet (UV) imaging sensor, or a near-infrared (NIR) imaging sensor, while the second imaging sensor may include an infrared (IR) imaging sensor, a time-of-flight (ToF) imaging sensor, a laser imaging detection and ranging (LIDAR) sensor, or a millimeter wave (MMW) imaging sensor. In other examples, the first imaging sensor may include a computed tomography (CT) scanner, magnetic resonance imaging (MRI) device, or other medical imaging device having a relatively higher resolution, definition, and/or contrast, and the second imaging sensor may include a positron emission tomography (PET) scanner, single-photon emission computed tomography (SPECT) scanner, ultrasound imaging device, or other medical imaging device having a relatively lower resolution, definition, and/or contrast. The first and the second imaging sensors may be configured to capture the target and the reference images that are 3-D volumetric or point-cloud images, according to some embodiments.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the figures.

DETAILED DESCRIPTION

Figure 1:
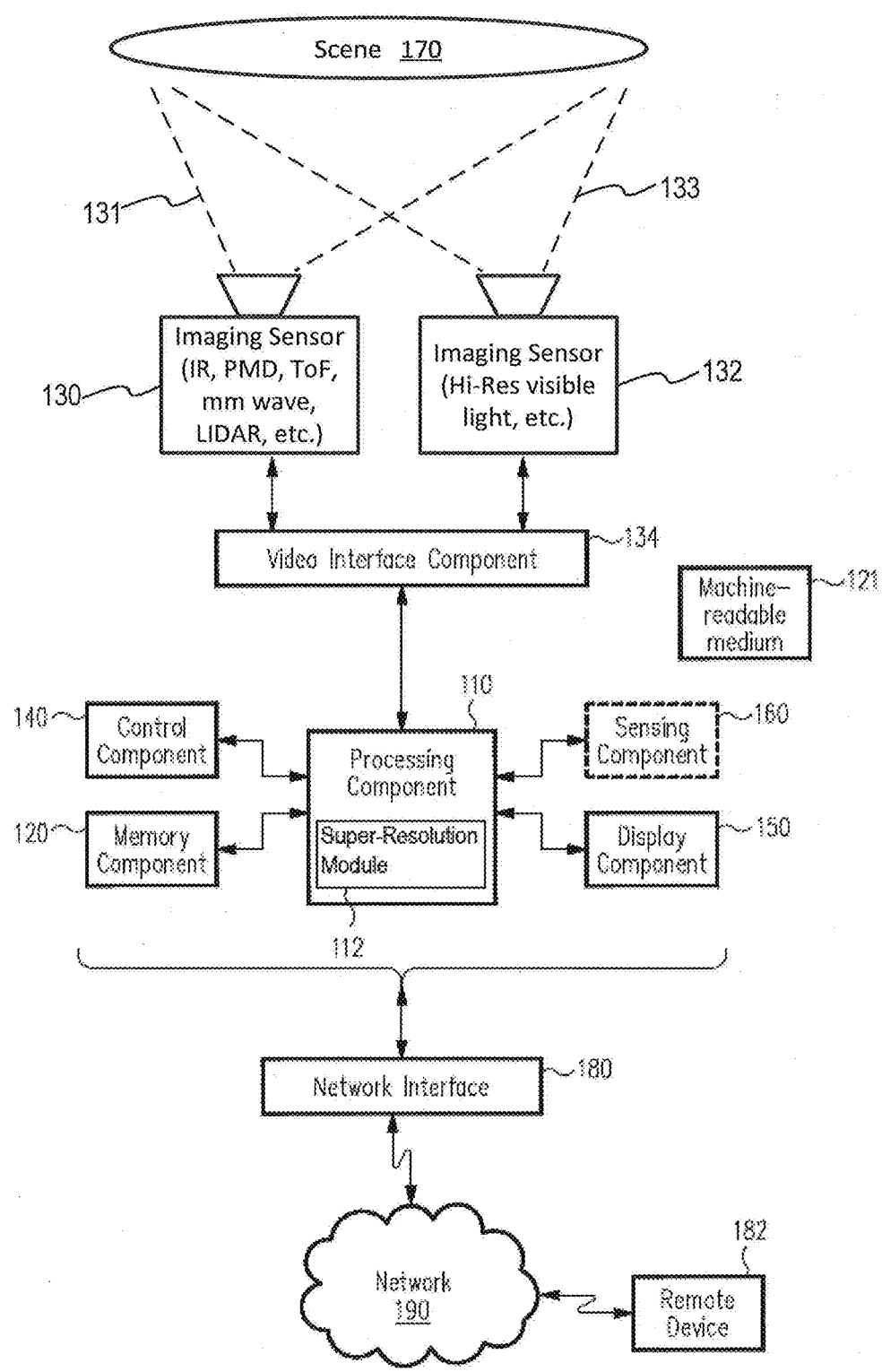
FIG. 1 illustrates a block diagram of an imaging system in accordance with an embodiment of the disclosure.

Various embodiments of the methods and systems disclosed herein may be used to provide resolution enhancement (also referred to herein as "super-resolution") of images (e.g., including still images and video frames) that have a lower resolution, lower definition, and/or lower signal-to-noise ratio (SNR) than desired. Such low resolution, definition, and/or SNR images may, for example, be captured by an imaging sensor or device that typically has a lower resolution, lower definition, and/or lower SNR than a CMOS, CCD, or other visible-light imaging sensor. For example, various imaging sensors and devices, such as infrared (IR) imaging sensors, photonic mixer devices (PMD) or other time-of-flight (ToF) imaging sensors, laser imaging detection and ranging (LIDAR) devices, and positron emission tomography (PET), single-photon emission computed tomography (SPECT), ultrasound imaging, or other medical imaging devices, operate in modalities or spectra that make it expensive or otherwise difficult to produce a high resolution, high definition, and/or high SNR output directly.

Systems and methods according to one or more embodiments of the disclosure can increase the resolution, definition, and/or SNR of such low fidelity (e.g., low resolution, definition, and/or SNR) images of a scene (to "super-resolve" images, as also referred to herein) by using "pilot" or "reference" images of the same scene captured in a higher resolution using a visible light imaging sensor or other imaging sensor capable of capturing a higher resolution image. For example, in one aspect, the systems and methods according to embodiments of the disclosure can determine adaptive-shape neighborhoods based on the reference image, and apply the adaptive-shape neighborhoods to a lower resolution "target" image to obtain a super-resolved version of the target image.

In particular, according to one or more embodiments, a neighborhood may be determined for each of a plurality of pixels in the reference image, where the shape (e.g., extent) of each neighborhood is adapted (e.g., varied) in response to structural information (e.g., object contours, edges, or other structural details) captured in the reference image. These adaptive-shape neighborhoods may then be applied to corresponding pixels of the "target" image to be super-resolved, and used for determining a local estimate (e.g., by local filtering, averaging, or other techniques to normalize or regularize the corresponding target image pixels) for a super-resolved version of the target image with respect to each adaptive-shape neighborhood as applied to the target image. Since the adaptive-shape neighborhoods for different pixel locations can overlap and thus comprise an overcomplete estimate of the super-resolved version of the target image or any portion thereof, the local estimates for the adaptive-shape neighborhoods can be aggregated to provide an estimate of the super-resolved version of the entire target image or any portion of the target image. In this way, for example, a super-resolved estimate of the target image may be obtained based on the adaptive-shape neighborhoods that adapt to the structural details captured in a higher resolution reference image.

In some embodiments, the super-resolved version of the target image obtained in this way may be compared with the original target image, and the difference between the two may be evaluated and injected back into the super-resolved version to constrain the super-resolved version to the original target image. This may be referred to herein as "back-projection" and may, for example, ensure that the pixel value (e.g., pixel value representing a radiometric observation such as a temperature or distance) of each pixel of the original target image is substantially preserved in the pixel values of the corresponding set of pixels (e.g., a corresponding macro-pixel) in the super-resolved version.

In some embodiments, the operations of determining adaptive-shape neighborhoods, determining local estimates with respect to the adaptive-shape neighborhoods, and aggregating the local estimates to provide a super-resolved version of the target image may be repeated iteratively in a coarse-to-fine manner, for example, by starting with bigger adaptive-shape neighborhoods (e.g., to produce smoother results) and progressively using smaller adaptive-shape neighborhoods to reveal finer structural details. It is also contemplated that the entire process can be repeated until a desired increase in resolution is achieved, using the obtained super-resolved version as the input target image for the next run of the process. For example, if the super-resolved version of the target image is obtained with 2× the original resolution in one run of the process, the process can be repeated twice to obtain 4× the original resolution, repeated three times to obtain 8× the original resolution, and so on.

Therefore, for example, various embodiments of methods and systems disclosed herein may be performed by, included in, or implemented as various devices and systems such as infrared imaging devices, range imaging devices, LIDAR devices, medical imaging devices, surveillance systems, image and video processing systems, or other systems or devices that may benefit from enhancement of the resolution, definition, and/or SNR of images and videos that are natively of low resolution, low definition, and/or low SNR, such as images and videos captured by an infrared imaging sensor, PMD imaging sensor, LIDAR imaging device, PET scanner, SPECT scanner, ultrasound imager or other imaging sensors operating in particular modalities or spectra. Super-resolved versions of such images and videos may provide easier-to-interpret, more visually pleasing, and more content-rich images and videos for viewing by users when displayed. In addition, super-resolved versions of such images and videos may improve the performance of various other video processing and analytics operations such as object detection, object identification, target tracking, segmentation, scene tracking, and other analytics operations when provided as an input to those operations.

Turning now to FIG. 1, a block diagram is illustrated of a system 100 for capturing and processing images and videos (e.g., video frames) in accordance with an embodiment of the disclosure. System 100 comprises, according to one implementation, a processing component 110, a memory component 120, a first imaging sensor 130, a second imaging sensor 132, a video interface component 134, a control component 140, a display component 150, a sensing component 160, and/or a network interface 180.

System 100 may represent an imaging device, such as a video and/or still camera, to capture and process images and/or videos of a scene 170. In this regard, the first imaging sensor 130 of system 100 may be configured to capture images (e.g., still and/or video images) of scene 170 in a particular spectrum or modality. For example, in some embodiments, the first imaging sensor 130 may include an IR imaging sensor configured to detect IR radiation in the near, middle, and/or far IR spectrum and provide IR images (e.g., IR image data or signal) representative of the IR radiation from scene 170. In one specific, not-limiting example, the first imaging sensor 130 may comprise a long-wave IR (LWIR) (e.g., a thermal IR) imaging sensor having a focal plane array (FPA) of detectors responsive to thermal IR radiation including LWIR radiation. An example of such a LWIR imaging sensor provided in a module can be found in U.S. patent application Ser. No. 14/101,258 filed on Dec. 9, 2013 and entitled "Infrared Camera System Architectures." Other suitable IR imaging sensors operating in near IR (NIR), short-wave IR (SWIR), mid-wave IR (MWIR), and/or LWIR may be also be utilized for desired applications of system 100.

The first imaging sensor 130 is not limited to an IR image sensor. Rather, in various embodiments, the first imaging sensor 130 may include a PMD imaging sensor or other ToF imaging sensor, LIDAR imaging device, millimeter imaging device, PET scanner, SPECT scanner, ultrasonic imaging device, or other imaging devices operating in particular modalities and/or spectra. Typically, the particular modalities and/or spectra in which these and IR imaging sensors operate make it expensive or difficult to produce high resolution, high definition, and/or high SNR output images, for example, when compared with a typical CMOS-based or CCD-based imaging sensors or other imaging sensors, imaging scanners, or imaging devices of different modalities.

In comparison, the second imaging sensor 132 of system 100 is configured to capture images of at least a portion of scene 170 in a higher resolution, higher definition, and/or higher SNR relative to the first imaging sensor 130. For example, in some embodiments, the second imaging sensor 132 may include a visible light imaging sensor configured to capture visible light images (e.g., visible light still images and/or video frames) having a higher resolution, and possibly a higher definition and/or higher SNR, than images captured by the first imaging sensor 130. The second imaging sensor 132 is not limited to a visible light imaging sensor, but rather may include any suitable imaging sensor that is configured to capture higher resolution, and possibly higher definition and/or higher SNR, images relative to the first imaging sensor. Thus, for example, various CMOS-based or CCD-based imaging sensors, ultraviolet (UV) imaging sensors, NIR imaging sensors, or other imaging sensors capable of producing higher resolution image outputs than the first imaging sensor 130 may be utilized for the second imaging sensor 132 in various embodiments. In some embodiments used for medical imaging, the first imaging sensor 130 may include a PET scanner, SPECT scanner, or ultrasonic imager, and the second imaging sensor 132 may include a computed tomography (CT) scanner or magnetic resonance imaging (MRI) device which typically has a higher resolution for a similar or same target image in the medical imaging application.

In one or more embodiments, relatively higher resolution images of at least a portion of scene 170 captured by the second imaging sensor 132 may be provided as "pilot" or "reference" images for enhancing the resolution of relatively lower resolution images captured by the first imaging sensor 130, as further discussed herein. The images captured by the first imaging sensor 130 may be provided as digital image data, for example, via an analog-to-digital converter included as part of the first imaging sensor 130 or other components of system 100. Similarly, the images captured by the second imaging sensor 132 may be provided as digital image data, for example, via an analog-to-digital converter included as part of the first imaging sensor 132 or other components of system 100. The images, or the digital image data corresponding to the images, comprise pixel values of the pixels belonging to the respective images. In some embodiments, analog-to-digital conversion, format conversion, and/or other interfacing operation may additionally or alternatively be provided by video interface component 134.

The images, or the digital image data corresponding to the images, provided by the first imaging sensor 130 and the second imaging sensor 132 may be associated with respective image dimensions (also referred to as pixel dimensions). An image dimension, or pixel dimension, generally refers to the number of pixels in an image, which may be expressed, for example, in width multiplied by height for two-dimensional images or otherwise appropriate for relevant dimension or shape of the image. Thus, images which are natively of lower resolution, such as those captured by the first imaging sensor 130, will typically have a smaller image dimension than higher resolution images, such as those captured by the second imaging sensor 132. Although natively low resolution images may be upscaled or upsampled to have a larger image dimension, it may be understood that upscaling or upsampling, without more, does not increase the native resolution or the definition (e.g., the image details) of the low resolution images.

The first and the second imaging sensors 130 and 132 are aligned or otherwise arranged such that the field-of-view 131 (FoV) of the first imaging sensor 130 at least partially overlaps the FoV 133 of the second imaging sensor 132. Thus, images captured by the first imaging sensor 130 depict at least a portion of scene 170 depicted in images captured by the second imaging sensor 132, or vice-versa. In some embodiments, the first and the second imaging sensors 130 and 132 may be structurally and/or mechanically aligned, for example, in accordance with techniques disclosed for aligning an infrared imaging module and a visible spectrum imaging module in U.S. patent application Ser. No. 14/138,058 filed Dec. 21, 2013 and entitled "Compact Multi-Spectrum Imaging with Fusion" or other appropriate techniques. In some embodiments, mechanical actuators may be provided to mechanically adjust the position and/or rotation of the first imaging sensor 130 and/or the second imaging sensor 132 based on the distance to scene 170, so as to compensate for parallax errors. In some embodiments, the FoVs 131 and 133 may be substantially the same (e.g., within an tolerable error range, such as +−5%), such that the first and the second imaging sensors capture a substantially same portion of scene 170. Alternatively or additionally for some embodiments, an image registration (image alignment) process may be performed (e.g., by processing component 110) to modify (e.g., by rotation, translation, cropping, warping, or other transforms) an image captured by the first imaging sensor 130, an image captured by the second imaging sensor 132, or both images as further discussed herein, so that the images captured by the first and the second imaging sensors 130 and 132 are substantially registered (e.g., aligned).

Processing component 110, according to various embodiments, comprises one or more of a processor, a microprocessor, a single-core processor, a multi-core processor, a microcontroller, a programmable logic device (PLD) (e.g., field programmable gate array (FPGA)), a digital signal processing (DSP) device, or other logic device that may be configured, by hardwiring, executing software instructions, or a combination of both, to perform various operations discussed herein for embodiments of the disclosure. For example, processing component 110 may include a super-resolution module 112, which may represent any suitable combination of hardware components and software instructions, configured to perform various operations to enhance the resolution of images as further discussed herein. Processing component 110 is configured to interface and communicate with various other components of system 100 to perform such operations. In one aspect, processing component 110 according to some embodiments may be configured to perform various system control operations (e.g., to control communications and operations of various components of system 100) and other image processing operations (e.g., data conversion, video analytics, noise suppression), as part of or separate from the operations to enhance the resolution of images.

It should be appreciated that super-resolution module 112 may, in some embodiments, be integrated in software and/or hardware as part of processing component 110, with code (e.g., software instructions and/or configuration data) for super-resolution module 112 stored, for example, in memory component 120. In some embodiments, a separate machine-readable medium 121 (e.g., a memory, such as a hard drive, a compact disk, a digital video disk, or a flash memory) may store the software instructions and/or configuration data which can be executed or accessed a computer (e.g., a logic device or processor-based system) to perform various methods and operations disclosed herein. In one aspect, machine-readable medium 121 may be portable and/or located separate from system 100, with the stored software instructions and/or data provided to system 100 by coupling the computer-readable medium to system 100 and/or by system 100 downloading (e.g., via a wired link and/or a wireless link) from computer-readable medium 121.

Memory component 120 comprises, in one embodiment, one or more memory devices configured to store data and information, including video image data and information. Memory component 120 may comprise one or more various types of memory devices including volatile and non-volatile memory devices, such as RAM (Random Access Memory), ROM (Read-Only Memory), EEPROM (Electrically-Erasable Read-Only Memory), flash memory, hard disk drive, and/or other types of memory. As discussed above, processing component 110 may be configured to execute software instructions stored in memory component 120 so as to perform method and process steps and/or operations described herein. Processing component 110 and/or video interface component 134 may be configured to store in memory component 120 images or digital image data captured by the first and the second imaging sensors 130 and 132. Processing component 110 may be configured to store processed (e.g., super-resolved, as discussed herein) still and video images in memory component 120.

Video interface component 134 may include, in some embodiments, appropriate input ports, connectors, switches, and/or circuitry configured to interface with external devices (e.g., a remote device 182 and/or other devices) to receive images (e.g., digital image data) generated by or otherwise stored at the external devices. The received images or image data may be provided to processing component 110. In this regard, the received images or image data may be converted into signals or data suitable for processing by processing component 110. For example, in one embodiment, video interface component 134 may be configured to receive analog video data and convert it into suitable digital data to be provided to processing component 110. In one aspect of this embodiment, video interface component 134 may comprise various standard video ports, which may be connected to a video player, a video camera, or other devices capable of generating standard video signals, and may convert the received video signals into digital video/image data suitable for processing by processing component 110. In some embodiments, video interface component 134 may also be configured to interface with and receive images (e.g., image data) from the first imaging sensor 130, the second imaging sensors 132, or both. In other embodiments, the first imaging sensor 130, the second imaging sensors 132, or both may interface directly with processing component 110.

Control component 140 comprises, in one embodiment, a user input and/or interface device, such as a rotatable knob (e.g., potentiometer), push buttons, slide bar, keyboard, and/or other devices, that is adapted to generate a user input control signal. Processing component 110 may be configured to sense control input signals from a user via control component 140 and respond to any sensed control input signals received therefrom. Processing component 110 may be configured to interpret such a control input signal as a value, as generally understood by one skilled in the art. In one embodiment, control component 140 may comprise a control unit (e.g., a wired or wireless handheld control unit) having push buttons adapted to interface with a user and receive user input control values. In one implementation, the push buttons of the control unit may be used to control various functions of system 100, such as autofocus, menu enable and selection, field of view, brightness, contrast, noise filtering, image enhancement, and/or various other features of an imaging system or camera.

Display component 150 comprises, in one embodiment, an image display device (e.g., a liquid crystal display (LCD)) or various other types of generally known video displays or monitors. Processing component 110 may be configured to display image data and information on display component 150. Processing component 110 may be configured to retrieve image data and information from memory component 120 and display any retrieved image data and information on display component 150. Display component 150 may comprise display circuitry, which may be utilized by the processing component 110 to display image data and information. Display component 150 may be adapted to receive image data and information directly from the first imaging sensor 130, the second imaging sensor 132, processing component 110, and/or video interface component 134, or the image data and information may be transferred from memory component 120 via processing component 110.

Sensing component 160 comprises, in one embodiment, one or more sensors of various types, depending on the application or implementation requirements, as would be understood by one skilled in the art. Sensors of sensing component 160 provide data and/or information to at least processing component 110. In one aspect, processing component 110 may be configured to communicate with sensing component 160. In various implementations, sensing component 160 may provide information regarding environmental conditions, such as outside temperature, lighting conditions (e.g., day, night, dusk, and/or dawn), humidity level, specific weather conditions (e.g., sun, rain, and/or snow), distance (e.g., laser rangefinder or time-of-flight camera), and/or whether a tunnel or other type of enclosure has been entered or exited. Sensing component 160 may represent conventional sensors as generally known by one skilled in the art for monitoring various conditions (e.g., environmental conditions) that may have an effect (e.g., on the image appearance) on the image data provided by imaging sensors 130 and/or 132.

In some implementations, sensing component 160 (e.g., one or more of sensors) may comprise devices that relay information to processing component 110 via wired and/or wireless communication. For example, sensing component 160 may be adapted to receive information from a satellite, through a local broadcast (e.g., radio frequency (RF)) transmission, through a mobile or cellular network and/or through information beacons in an infrastructure (e.g., a transportation or highway information beacon infrastructure), or various other wired and/or wireless techniques.

In various embodiments, various components of system 100 may be combined and/or implemented or not, as desired or depending on the application or requirements. In one example, processing component 110 may be combined with memory component 120, the first imaging sensor 130, the second imaging sensor 132, video interface component 134, display component 150, network interface 180, and/or sensing component 160. In another example, processing component 110 may be combined with the first imaging sensor 130 and/or the second imaging sensor 132, such that certain functions of processing component 110 are performed by circuitry (e.g., a processor, a microprocessor, a logic device, a microcontroller, etc.) within the first imaging sensor 130 and/or the second imaging sensor 132.

Furthermore, in some embodiments, various components of system 100 may be distributed and in communication with one another over a network 190. In this regard, system 100 may include network interface 180 configured to facilitate wired and/or wireless communication among various components of system 100 over network. In such embodiments, components may also be replicated if desired for particular applications of system 100. That is, components configured for same or similar operations may be distributed over a network. Further, all or part of any one of the various components may be implemented using appropriate components of a remote device 182 (e.g., a conventional digital video recorder (DVR), a computer configured for image processing, and/or other device) in communication with various components of system 100 via network interface 180 over network 190, if desired. Thus, for example, all or part of processor 110, all or part of memory component 120, and/or all of part of display component 150 may be implemented or replicated at remote device 182, and configured to perform resolution enhancement of images as further described herein. In some embodiments, system 100 may not comprise imaging sensors (e.g., imaging sensors 130 and/or 132), but instead receive images or image data from imaging sensors located separately and remotely from processing component 110 and/or other components of system 100. It will be appreciated that many other combinations of distributed implementations of system 100 are possible, without departing from the scope and spirit of the disclosure.

Figure 2:
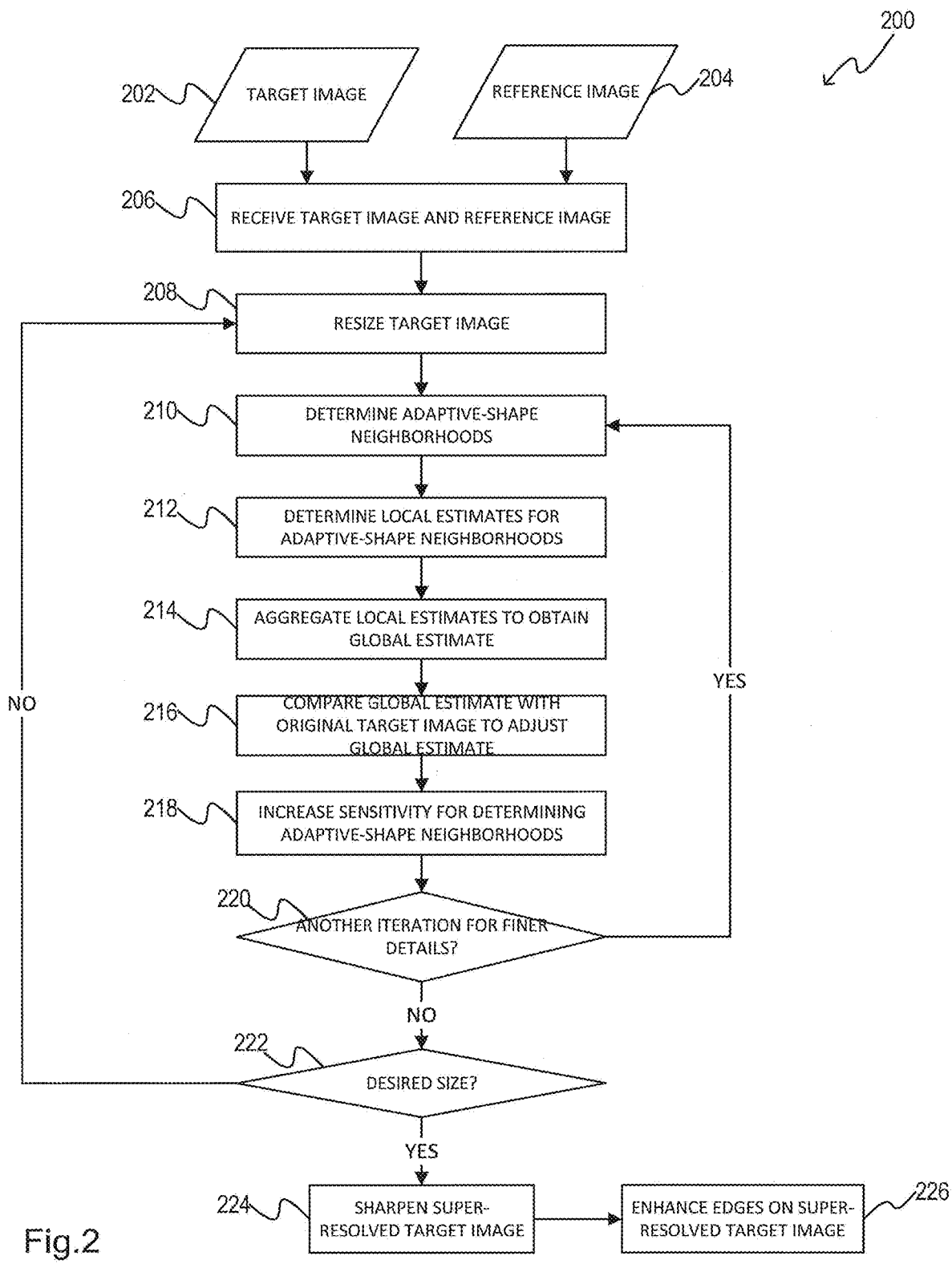
FIG. 2 illustrates a flow diagram of a process to enhance image resolution in accordance with an embodiment of the disclosure.

FIG. 2 illustrates a flow diagram of a process 200 to enhance image resolution in accordance with an embodiment of the disclosure. Process 200 may be performed by various embodiments of system 100, for example. However, it should be appreciated that system 100 and various components thereof are identified only for purposes of giving examples, and that any other suitable system may be utilized to perform all or part of process 200. It should also be appreciated that any block, sub-bloc, step, sub-step, or sub-process process 200 may be combined and/or performed in an order or arrangement different from the embodiment illustrated by FIG. 2.

At block 206, a target image 202 and a reference image 204 are received, for example, at processing component 110 from imaging sensors 130 and 132, or from externally captured and/or stored images or videos via video interface component 134. As discussed, target image 202 is an image (e.g., digital image data) that is to be super-resolved (e.g., have its resolution, definition, and/or SNR increased), and may be captured by an IR imaging sensor, PMD or other ToF imaging sensor, LIDAR imaging device, millimeter wave imaging sensor, or other imaging sensors operating in modalities or spectra that make it expensive or otherwise difficult to produce a high resolution, high definition, and/or high SNR output natively. In one example, target image 202 may be a LWIR image captured in a relatively low native resolution such as 80×60, 160×120, 320×240, or other resolution.

As also discussed, reference image 204 (or pilot image 204) is an image (e.g., digital image data) that has a higher resolution relative to target image 202, and may, for example, be captured by a visible light, UV, or NIR imaging sensor, or a CCD-based or CMOS-based imaging sensor that is typically capable of outputting higher resolution, higher definition, and/or higher SNR images than target image 202. In one example, reference image 204 may be a greyscale or color visible light image captured in a higher native resolution, such as 640×480 or higher, than target image 202. In some embodiments, only a greyscale (e.g., luminance or intensity) channel may be extracted and used from a color visible light image captured by a visible light imaging sensor.

Target image 202 and reference image 204 may both depict a same scene (e.g., scene 170). More specifically, the FoV associated with target image 202 at least partially overlaps the FoV associated with reference image 204, such that target image 202 depicts at least a portion of the scene captured in reference image 204, or vice-versa. In some embodiments, as above in connection with imaging sensors 130 and 132 of system 100, target image 202 and reference image 204 may depict a substantially a same portion of a scene, for example, by mechanical and/or structural alignment of imaging sensors 130 and 132. In other words, in these embodiments, target image 202 and reference image 204 as received may be substantially registered (e.g., aligned) to each other. In some embodiments, for example in case target image 202 and reference image 204 are not sufficiently registered as received, block 206 may include performing an image registration (image alignment) process to modify target image 202, reference image 204, or both to spatially align (e.g., register) the two images so that the two image depict substantially a same portion of the scene (e.g., within an tolerable error range, such as +−5%). For example, affine transforms, such as rotation, translation, cropping, and non-rigid transforms, such as warping and deformation, can be applied to spatially align the two images. Such transforms may be determined by comparing intensity patterns in the two images or by detecting and comparing corresponding features in the two images, as examples according to various embodiments. As further discussed herein, process 200 according to some embodiments can further correct residual image registration errors after resolution enhancement of target image 202.

In embodiments for medical imaging, target image 202 and reference image 204 may depict a similar or same cross section view (e.g., a two-dimensional image, also referred to as a 2-D image) of a patient's body, or a similar or same volumetric view (e.g., a three-dimensional image, also referred to as a 3-D image) of a patient's body. Target image 202 and reference image 204 may be captured of a patient using medical imaging devices of different modalities, and aligned by appropriate processing so that they depict a substantially same sectional view or volumetric view of the patient's body. Further in this regard, for some embodiments, target image 202 and reference image 204 may be higher dimensional (e.g., 3-D or any n-dimensional) volumetric or point-cloud images, and relevant operations of method 200 of FIG. 2 may be performed with respect to three axes (x, y, and z axes) or any n-dimensional coordinate system to enhance three or higher dimensional target images.

Target image 202 and reference image 204 may be associated with respective image dimensions and provided as digital image data comprising pixel values for pixels belonging to respective images, as discussed above in connection with imaging sensors 130 and 132 of system 100. As may be understood, each pixel of reference image 204 (also referred to herein as reference image pixel) may be identified by a corresponding pixel coordinate (e.g., pixel location, pixel index) within the associated image dimension. For example, for a reference image having an image dimension of 160×120 pixels, each of the 160×120 pixels may be identified by a pixel coordinate comprising the pixel location in the x-axis or width (e.g., between 1 to 160 or 0 to 159) and the pixel location in the y-axis or height (e.g., between 1 to 120 or 0 to 119) of the reference image.

In some embodiments, the receiving of target image 202 and reference image 204 at block 206 may include capturing target image 202 using an imaging sensor (e.g., imaging sensor 130) such as an IR imaging sensor, PMD or other ToF imaging sensor, LIDAR imaging device, millimeter wave imaging sensor, PET scanner, SPECT scanner, ultrasound imager, or other imaging sensors that produce relatively lower resolution, lower definition, and/or lower SNR native output images, and capturing reference image 204 using another imaging sensor (e.g., imaging sensor 132) such as a visible light, UV, or NIR imaging sensor, a CCD-based or CMOS-based imaging sensor, or MRI device or CT scanner that is typically capable of outputting higher resolution, higher definition, and/or higher SNR images than target image 202. In some embodiments, the capturing of target image 202 and the capturing of reference image 204 may be performed substantially at the same time or within a certain interval (e.g., determine based on motion present in scene 170, motion of imaging sensors, or relative motion between scene and imaging sensors) so that the scene remains sufficiently unchanged to allow reference image 204 to be used for enhancing resolution of target image 202.

At block 208, target image 202 may be resized to have a larger image dimension. In various embodiments, upscaling (e.g., by bilinear interpolation), upsampling, or other linear, higher-order, or non-linear interpolation techniques may be performed on target image 202 to resize target image 202 to a larger image dimension than its native image dimension. For example, a target image 202 having a native resolution and image dimension of 80×60 may be resized by bilinear interpolation to have a larger image dimension of 160×120. In this example, each pixel of the resized target image 202 (also referred to herein as target image pixel) may then be identified by a corresponding pixel coordinate comprising one of 160 positions in the x-axis or width and one of 120 positions in the y-axis or height.

In some embodiments, reference image 204 may be downscaled, downsampled, or otherwise resized to match the image dimension of the resized target image 202, in case reference image 204 has a larger image dimension than the resized target image 202. Continuing with the example above, a reference image having a native resolution and image dimension of 640×480 may be downscaled to match the image dimension of 160×120 of the resized target image. Since target image 202 and reference image 204 are spatially registered such that the two images both depict a substantially same scene as discussed above for block 206, each pixel coordinate for the pixels of reference image 204 can also map to a pixel in the resized target image 202 that corresponds to a substantially same location in the scene. For example, a pixel coordinate of (100, 80) that identifies a reference image pixel for a reference image downscaled to 160×120 may also identify a corresponding target image pixel of a target image upscaled to 160×120, where both the reference image pixel and the target image pixel depict a substantially same location in the scene.

Alternatively in some embodiments, reference image 204 may not be downscaled, downsampled, or otherwise resized to match the resized target image 202, but instead each pixel coordinate for the pixels of reference image 204 may be translated to map to a pixel in the resized target image 202. For example, four neighboring pixel coordinates (e.g., all belonging to a same macro-pixel) in a reference image that has an image dimension of 320×240 may be mapped to one pixel in a resized target image that has an image dimension of 160×120.

At block 210, adaptive-shape neighborhoods are determined based on reference image 204. In particular, a neighborhood may be determined for each pixel (e.g., at each pixel coordinate) in reference image 204, where the shape (e.g., extent) of each neighborhood is adapted (e.g., varied) in response to structural information (e.g., object contours, edges, or other structural details) captured in reference image 204. For example, according to various embodiments, each adaptive-shape neighborhood extends from each reference image pixel coordinate to include those reference image pixels within the shape-adaptive neighborhood that meet a given regularity condition (e.g., smoothness). In other words, the extent or shape of each adaptive-shape neighborhood from a given reference image pixel coordinate as the center point is determined based on the regularity (e.g., smoothness) of reference image pixels at and surrounding the given image pixel coordinate.

Figure 3A:
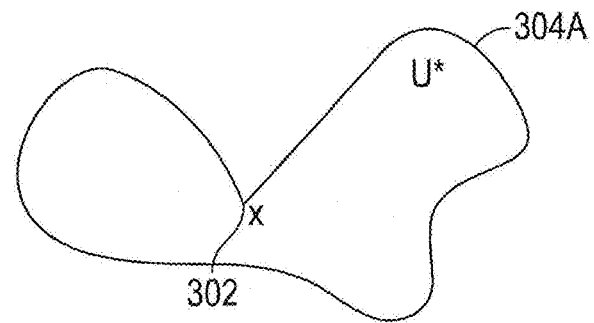
FIGS. 3A-3C illustrate adaptive-shape neighborhoods determined in the process of FIG. 2, in accordance with various embodiments of the disclosure.
Figure 3B:
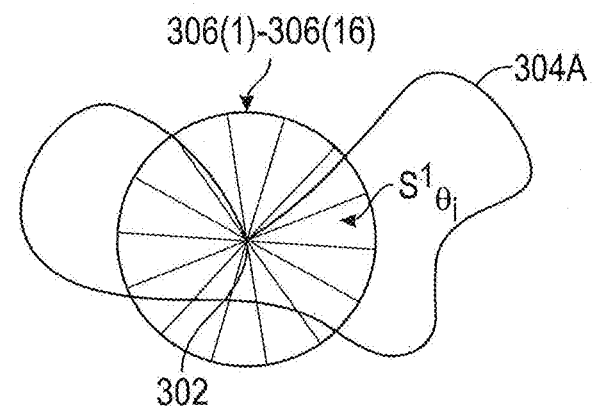
Figure 3C:
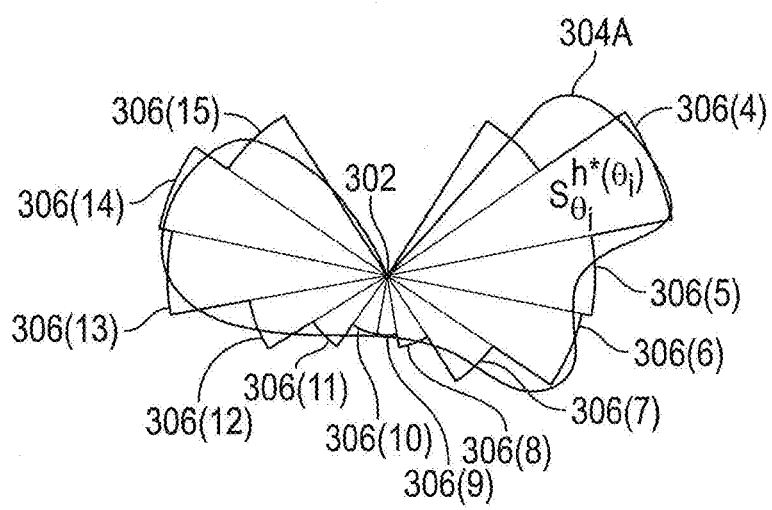

Referring also to FIG. 3A-3C, examples of an adaptive-shape neighborhood determined for a given reference image pixel coordinate 302 (also labeled x) are illustrated in accordance with embodiments of the disclosure. In general, according to various embodiments of the disclosure, an adaptive-shape neighborhood 304A (also labeled U*) for reference image pixel location 302 extends anisotropically (e.g., having different extents for different directions) such that those reference image pixels within adaptive-shape neighborhood 304A meet a regularity condition, as shown in FIG. 3A. For example, the reference image pixels belonging to adaptive-shape neighborhood 304A may have pixel values that are regular or similar according to a statistical criterion such that those pixels may appear smooth without abrupt changes (e.g., due to object contours, edges, or other structural details). In this regard, adaptive-shape neighborhood 304A adapts its shape (e.g., extent) in response to structural information (e.g., object contours, edges, or other structural details or change points), and thus reveal fine structural details and elements around reference image pixel location 302.

FIGS. 3B and 3C illustrate how an adaptive-shape neighborhood may be determined (e.g., approximated) as a combination of adaptive-scale directional windows 306(1) through 306(16), according to one or more embodiments of the disclosure. In the example of FIGS. 3B and 3C, adaptive-scale directional windows 306(1) through 306(16) may be considered for sixteen directions from reference image pixel location 302, and each of such adaptive-scale directional windows 306(1) through 306(16) may individually (e.g., anisotropically) adapt its scale (e.g., extent) so that reference image pixels within each adaptive-scale directional window meet a given regularity condition. Thus, a combination of adaptive-scale directional windows 306(1) through 306(16) anisotropically scaled in such a manner as shown in FIG. 3C can approximate adaptive-scale neighborhood 304A of FIG. 3A (adaptive-scale directional windows 306(1), 306(2), and 306(16) are not explicitly identified in FIG. 3C because they may have a scale of 1, i.e., do not extend from reference image pixel location 302). In one or more embodiments, the scale (e.g., extent) of each adaptive-scale directional windows 306(1) through 306(16) may be determined based on the scale (e.g., extent) of a local polynomial approximation (LPA) kernel that provides the best approximation or estimate among a set of varying-scale directional-LPA convolution kernels, using a statistical method such as the intersection of confidence intervals (ICI) method, in a similar manner as further described herein for some embodiments of the disclosure.

It should be appreciated the adaptive-scale directional windows are shown in FIGS. 3B and 3C as sections of concentric circles equally divided into sixteen directions for purposes of giving examples only, and that the number of directions and the shape of the windows shown in FIGS. 3B and 3C are not limiting and can be of different numbers and shapes without departing from the spirit and scope of the disclosure. Also, it is contemplated that isotropically extending adaptive-shape neighborhoods, rather than anisotropically extending ones as shown, may be used for some embodiments of the disclosure.

Figure 3D:
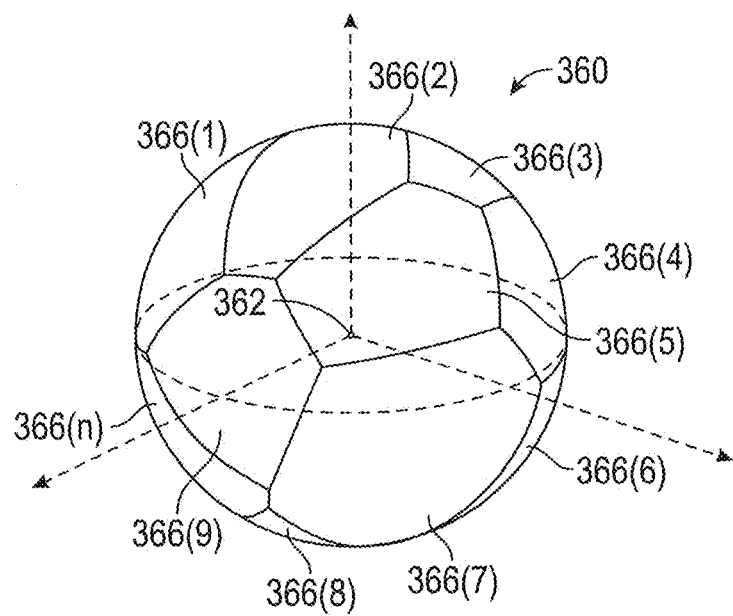
FIGS. 3D-3E illustrate adaptive-scale directional sectors for determining adaptive-shape neighborhoods in three-dimensional images, in accordance with various embodiments of the disclosure.

FIG. 3D illustrates adaptive-scale directional windows 366(1) through 366(n) shown for a unit sphere 360 (also referred to adaptive-scale directional sectors 366(1) through 366(n)), which may be scaled and combined to form an adaptive-shape neighborhood for 3-D volumetric images (e.g., captured by a medical imaging device such as a PET scanner, SPECT scanner, ultrasound imager, MRI device, or CT scanner) or 3-D point-cloud images (e.g., captured by a LIDAR, or PMD or other ToF imaging sensor), in accordance with an embodiment of the disclosure. Similar to adaptive-scale directional windows 306(1) through 306(16) but applied to a 3-D volumetric or point-cloud images, each of the adaptive-scale directional sectors 366(1) through 366(n) may individually (e.g., anisotropically) adapt its scale (e.g., extent) so that reference 3-D volumetric image pixels (also referred to as "voxels") or reference 3-D point-cloud image points that are within each adaptive-scale directional sector from a reference image voxel or point location 362 meet a given regularity condition.

Figure 3E:
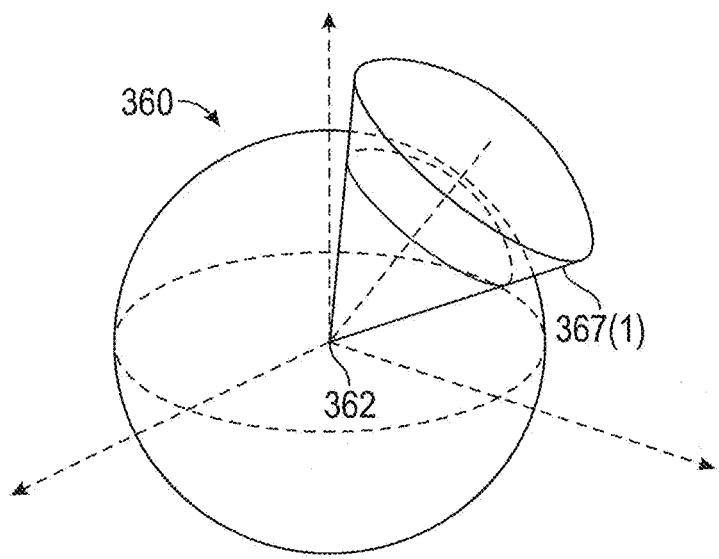

In this regard, adaptive-scale directional sectors 366(1) through 366(n) may comprise a finite family of non-overlapping contractible bodies. For example, such a finite family of non-overlapping contractible bodies may include a Voronoi tiling that covers the entire sphere as shown in the example of FIG. 3D. In other examples according to some embodiments, adaptive-scale directional sectors need not cover the entire sphere, and instead comprise a finite number of cones (e.g., an adaptive-scale directional sector 367(1)) pointing at different directions and covering only a part of the 3-D neighborhood for the reference image voxel location 362, as shown in the example of FIG. 3E.

Figure 4:
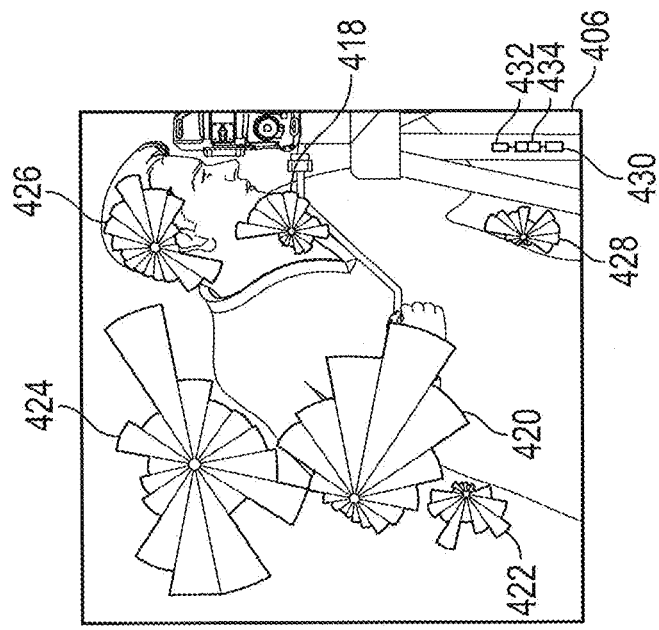
FIG. 4 illustrates adaptive-shape neighborhoods determined as a combination of adaptive-shape directional windows, in accordance with an embodiment of the disclosure.
Figure 4:
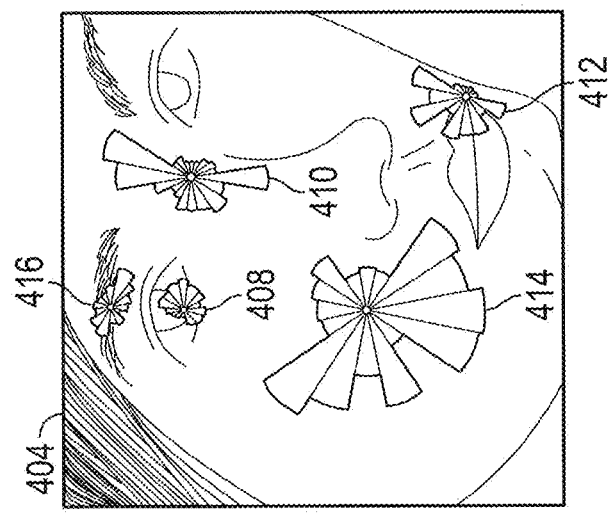
Figure 4:
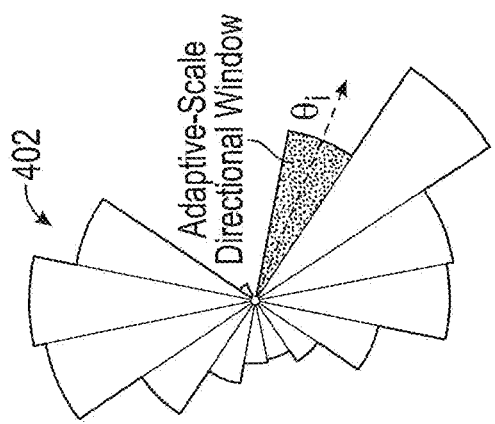

FIG. 4 illustrates adaptive-shape neighborhoods 408-430 determined for some selected reference image pixel coordinates in example two-dimensional reference images 404 and 406, in accordance with an embodiment of the disclosure. In FIG. 4, adaptive-shape neighborhoods 408-430 may be determined as a combination of adaptive-shape directional windows, as discussed above for in FIGS. 3B and 3C and illustrated for example as adaptive-shape neighborhood 402. As shown, each of the adaptive-shape neighborhoods 408-430 extends from a corresponding reference image pixel coordinate to include those reference image pixels that appear regular (e.g., smooth), and adapts its boundary in response to changes due to object contours, edges, or other structural details. Although FIG. 4 shows adaptive-shape neighborhoods determined for a few selected reference image pixel coordinates as examples, block 210 of process 200 may determine adaptive-shape neighborhoods for reference image pixel coordinates of some selected areas or all of reference image 204. As may also be appreciated, adaptive-shape neighborhoods for different reference image pixel coordinates, such as those pixel coordinates that are close to one another, may often overlap.

Figure 5:
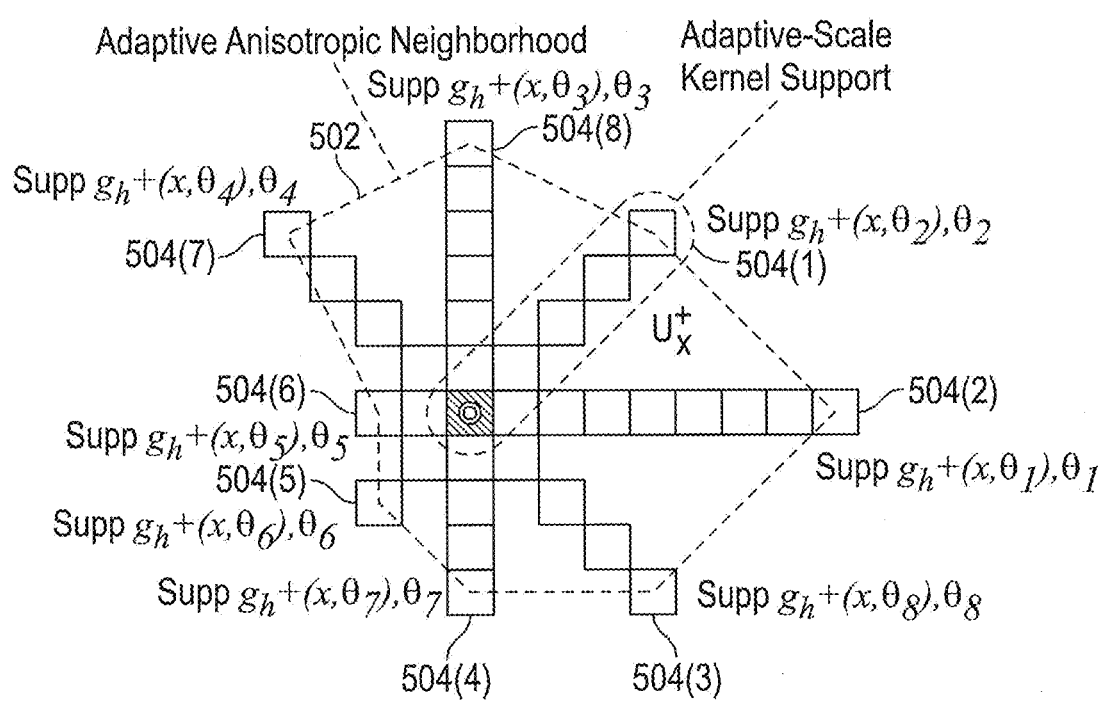
FIG. 5 illustrates an adaptive-shape neighborhood determined using line-wise extents, in accordance with an embodiment of the disclosure.

In some embodiments, adaptive-shape neighborhoods may be determined efficiently by using narrow one-dimensional line-wise kernels for a predetermine set of directions. For example, FIG. 5 illustrates an adaptive-shape neighborhood 502 (also referred to as adaptive anisotropic neighborhood 502) determined using the extents (e.g., lengths) of adaptive-scale, one-dimensional line-wise kernel supports 504(1)-504(8) (also referred to as line-wise supports or adaptive-scale kernel supports) in eight directions, in accordance with an embodiment of the disclosure. More specifically, an extent (e.g., length) of each of the line-wise supports 504(1)-504(8) (or simply referred to as a line-wise extent) is first determined such that those reference image pixels that belong to the line-wise support meet a predetermined regularity (e.g., smoothness) condition (e.g., criterion), then adaptive-shape neighborhood 502 may be constructed as a polygonal hull of the determined line-wise extents.

Figure 6A:
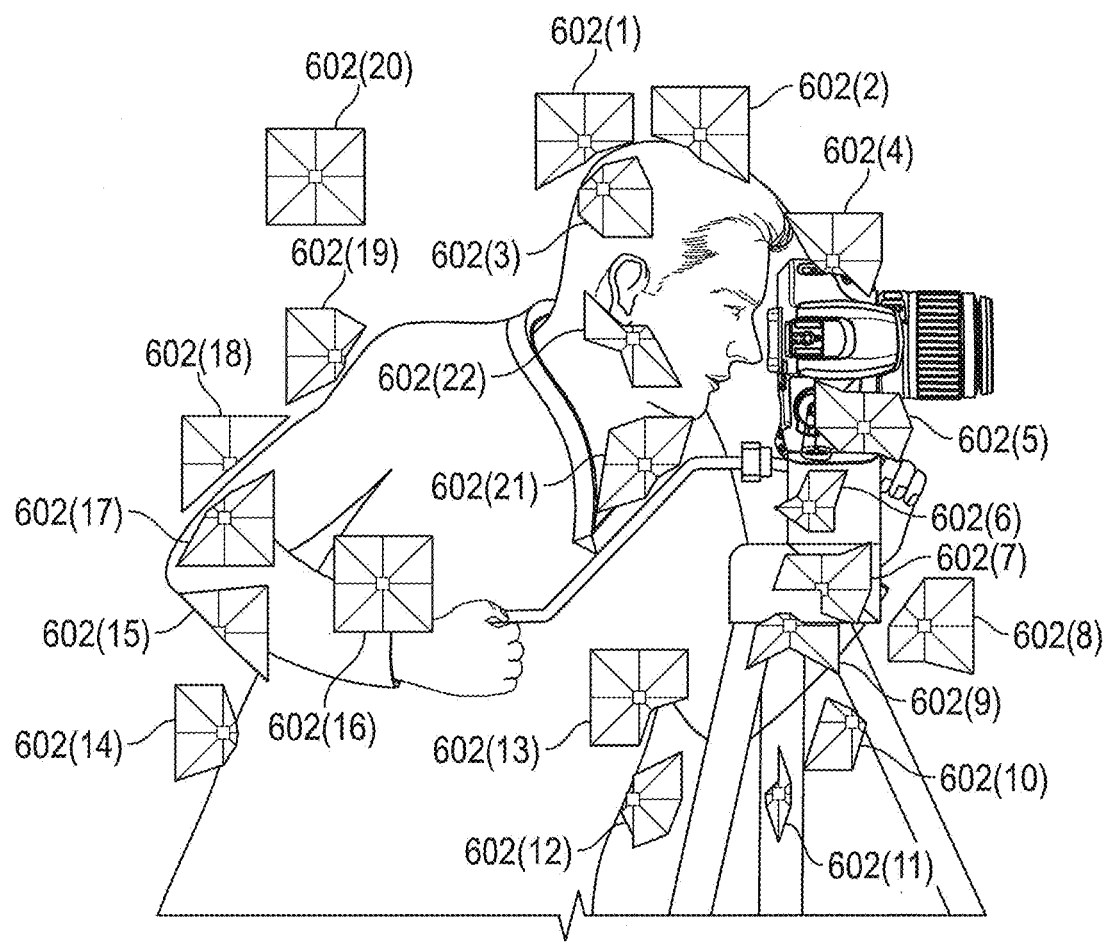
FIG. 6A illustrates adaptive-shape neighborhoods determined using line-wise extents for selected pixel coordinates of an example two-dimensional reference image, in accordance with an embodiment of the disclosure.

FIG. 6A illustrates examples of adaptive-shape neighborhoods 602(1)-602(22) determined in such a manner for twenty-two selected reference image pixel coordinates in reference image 406 of FIG. 4, in accordance with an embodiment of the disclosure. As shown, although adaptive-shape neighborhoods 602(1)-602(22) are determined as polygonal hulls of star-shaped line-wise extents, they are still effective at adapting its boundary in response to changes due to object contours, edges, or other structural details.

However, for these embodiments, the actual adaptive-shape neighborhoods need not be constructed or otherwise determined from the line-wise extents until the neighborhoods are applied to target image 202 to determine local estimates. It should also be understood that although the line-wise extents are determined for eight directions in the examples above, more or less than eight directions may be used as desired for embodiments.

Figure 6B:
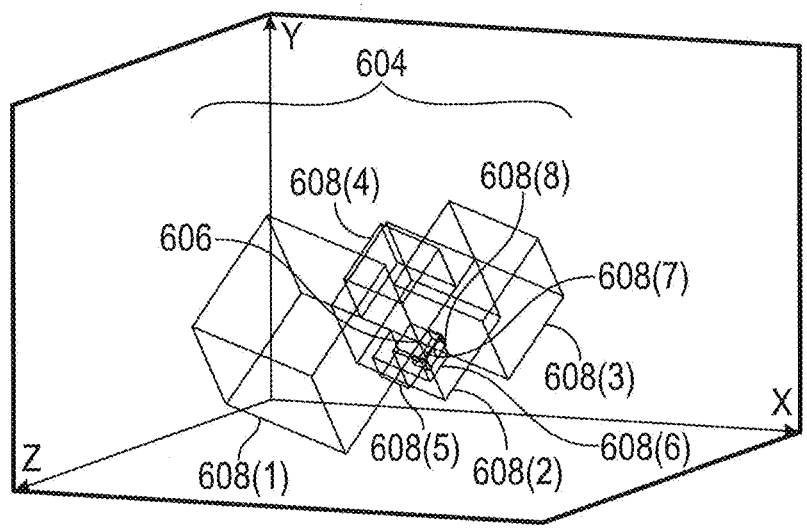
FIG. 6B illustrates an adaptive-shape neighborhood determined using adaptive-scale cubes for a selected point of an example three-dimensional point-cloud reference image, in accordance with an embodiment of the disclosure.

Such efficient determination of adaptive-shape neighborhoods may also be performed for 3-D or higher dimensional cases as well, according to some embodiments. For example, FIG. 6B illustrates an adaptive-shape neighborhood 604 determined for a reference point 606 of a 3-D point-cloud reference image in accordance with an embodiment of the disclosure. In this example, adaptive-shape neighborhood 604 of reference point 606 is determined using the extents of adaptive-scale 3-D cubes 608(1) through 608(8) which extend relative to reference point 606 to adapt their sizes in 8 octants according to a predetermined regularity condition. In other embodiments for a 3-D volumetric image case, line-wise kernel supports may be used similar to adaptive-shape neighborhoods 502 and 602, but placed in a 3-D space to form the supports for a polyhedral hull that corresponds to the 3-D adaptive-shape neighborhood from a reference voxel location.

As briefly discussed above, the extent (e.g., scale, length) of each line-wise adaptive-scale kernel support (or adaptive-scale directional windows in some embodiments) may be determined from the length or scale of a support that provides the best approximation of the reference image pixel among a set of varying-scale kernel supports. For example, according to one or more embodiments, the length or scale of a line-wise LPA kernel $g_{h^+(x,\theta_k),\theta_k}$ that provides the best approximate among a set of line-wise LPA kernels $\{g_h \theta_k\}_{h \in H}$ may be chosen for each direction $\theta_k$. The selection of the best-approximating LPA kernel $g_{h^+(x,\theta_k),\theta_k}$ may involve a statistical method, such as the ICI method.

Figure 7:
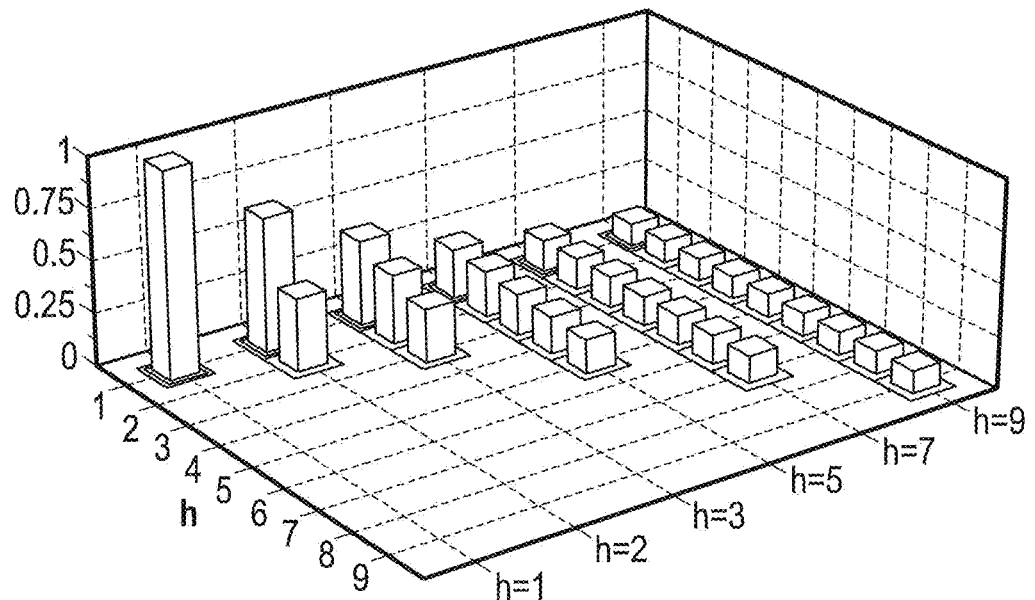
FIG. 7 illustrates line-wise LPA kernels for determining line-wise extents of an adaptive-shape neighborhood, in accordance with an embodiment of the disclosure.

FIG. 7 illustrates an example of such line-wise LPA kernels for direction $\theta_1=0$ for a set of scales (e.g., lengths) $H=\{1, 2, 3, 5, 7, 9\}$, in accordance with an embodiment of the disclosure. The diagonal kernels, such as for direction $$\theta_2 = \frac{\pi}{4},$$

may be obtained by slanting the corresponding horizontal kernels, such as the line-wise kernel $\{g_h, \theta_1\}_{h \in H}$. The kernels for the remaining six directions may be obtained by repeated 90-degrees rotations of these two sets, for example, if the line-wise extents are to be determined for eight directions. As these kernels are line-wise (one-dimensional) kernels, they may be understood as vectors of length h E H={1, 2, 3, 5, 7, 9}, as shown in FIG. 7. The height of the bars in FIG. 7 represents the value of each component of each vector. The value of each component may be determined, for example, by the polynomial order of the LPA. The example set of FIG. 7 comprises mixture-order kernels with a mixture of 0-th and $1^{st}$ order LPA.

To select the best-approximating line-wise LPA kernel among the set of line-wise LPA kernels for a reference image pixel coordinate according to some embodiments, the reference image pixels along the direction and length of the line-wise LPA kernels are convoluted with the line-wise LPA kernels to provide a set of LPA estimates, and the line-wise LPA kernel that produces the best LPA estimate for the reference image pixel at the coordinate may be selected. The selection of the best LPA estimate, and hence the length (e.g., extent, scale) of the line-wise LPA kernel, may be performed using a statistical method.

For example, in some embodiments, the ICI method may be adapted and utilized for the selection. For a more formal illustration according to some embodiments, consider the intersection of confidence interval (ICI) $I_j = \cap_{i=1}^{+} D_i$, where $$D_i = [\hat{y}h_i(x) - \Gamma \sigma_{\hat{y}h_i}(x), \hat{y}h_i(x) + \Gamma \sigma_{\hat{y}h_i(x)}] \quad (\text{Equation 1}),$$

where $\sigma_{\hat{y}h_i(x)} = \text{std}\{\hat{y}h_i(x)\}$ is the standard deviation of the LPA estimate $\hat{y}h_i(x)$, and where $\Gamma>0$ is a threshold (or sensitivity) parameter. The standard deviation of the LPA estimate $\hat{y}h_i(x)$ may be calculated from the $l^2$-norm of the corresponding kernel. Then we may determine an index $j^+$ for $\hat{y}h_i(x)$, which is the largest of the indexes j for which $I_j$ is non-empty, $I_{j^+} \neq \emptyset$, and $I_{j^++1} = \emptyset$. The LPA kernel $h_{j^+}$ is than selected as the one that produces the "best" estimate among the set of LPA kernels. In other words, the selected LPA kernel $h_{j^+}$ may be the lengthiest among the set of LPA kernels that provides an acceptable approximation of the reference image pixel at the coordinate according to the ICI method. The selected LPA kernel $h_{j^+}$ may also be referred to herein as an "adaptive scale $h^+(x)$," $h^+(x) = h_{j^+}$.

Figure 8:
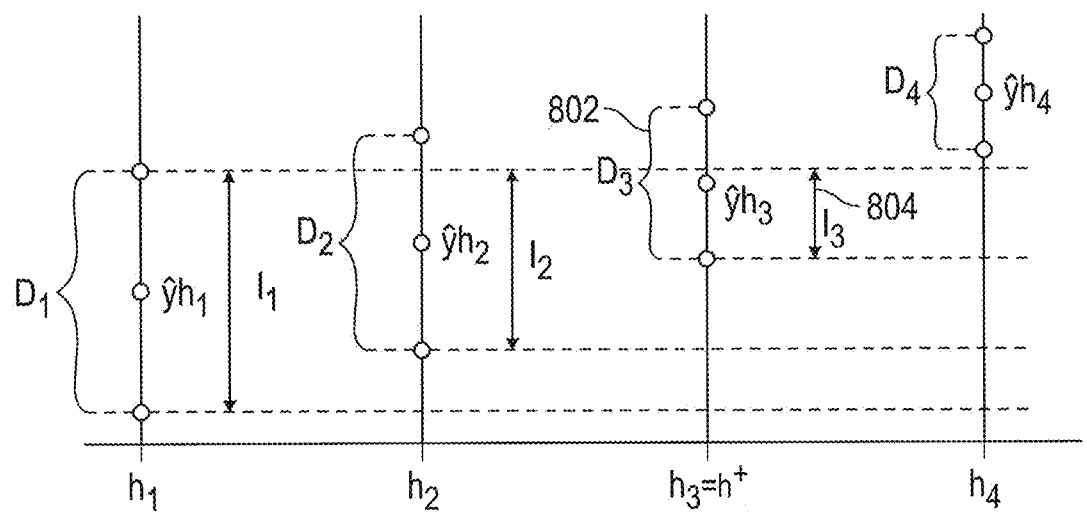
FIG. 8 illustrates how an intersection of confidence intervals method may be used to select an optimal line-wise LPA kernel, in accordance with an embodiment of the disclosure.

An example illustration of such selection using the ICI method is given in FIG. 8 in accordance with an embodiment of the disclosure. In the example of FIG. 8, the confidence interval 802 (also labeled $D_3$) for j=3 has an intersection 804 (also labeled $I_3$) with previous confidence intervals $D_1$ and $D_2$ (i.e., $I_3 \neq \emptyset$), but for j=4 there is no intersection with previous confidence intervals (i.e., $I_{3+1} = I_4 = \emptyset$). Thus, the LPA kernel $h_3$, and its line-wise extent (length or scale) of 3 can be selected in this example. As may be appreciated, as the index j increase, the LPA kernels increase in length, and thus the standard-deviations decrease and the confidence intervals shrink. In this regard, the LPA estimates are tested in the intersections with progressively lower variance, and the index $j^+$ is selected based on a rationale that the estimation bias may not be too large as long as the intersections are non-empty.

Note that the confidence intervals are also responsive to the threshold parameter $\Gamma$. As the threshold parameter $\Gamma$ is decreased, the confidence intervals decrease. Smaller confidence intervals may lead to selection of smaller LPA kernels as the adaptive scale, which in turn produces smaller adaptive-shape neighborhoods. In this regard, the threshold parameter $\Gamma$ may be varied to adjust the sensitivity for testing the regularity (e.g., smoothness) condition in determining the adaptive-shape neighborhoods. For the threshold parameter $\Gamma$ as used in equation 1 above, decreasing the threshold parameter $\Gamma$ may effectively result in an increased sensitivity for regularity within adaptive-shape neighborhoods, which may lead to smaller-sized adaptive-shape neighborhoods that are adapted to reveal finer details in reference images.

As discussed above, an adaptive-shape neighborhood associated with a pixel coordinate then be a polygonal hull of the determined line-wise extents (e.g., lengths of line-wise adaptive-scale kernel supports) for a predetermined set of directions from the pixel coordinate. In some embodiments, such a polygonal hull may be obtained efficiently by a combination of pre-calculated (e.g., to have pixel coordinates pre-determined), non-overlapping triangles (e.g., triangular binary stencils), each of which is associated with a pair of possible line-wise adaptive-scale kernel supports. These pre-calculated triangular stencils may be used to determine which pixel coordinates belong to the adaptive-shape neighborhood as determined using the line-wise extents.

Figure 9:
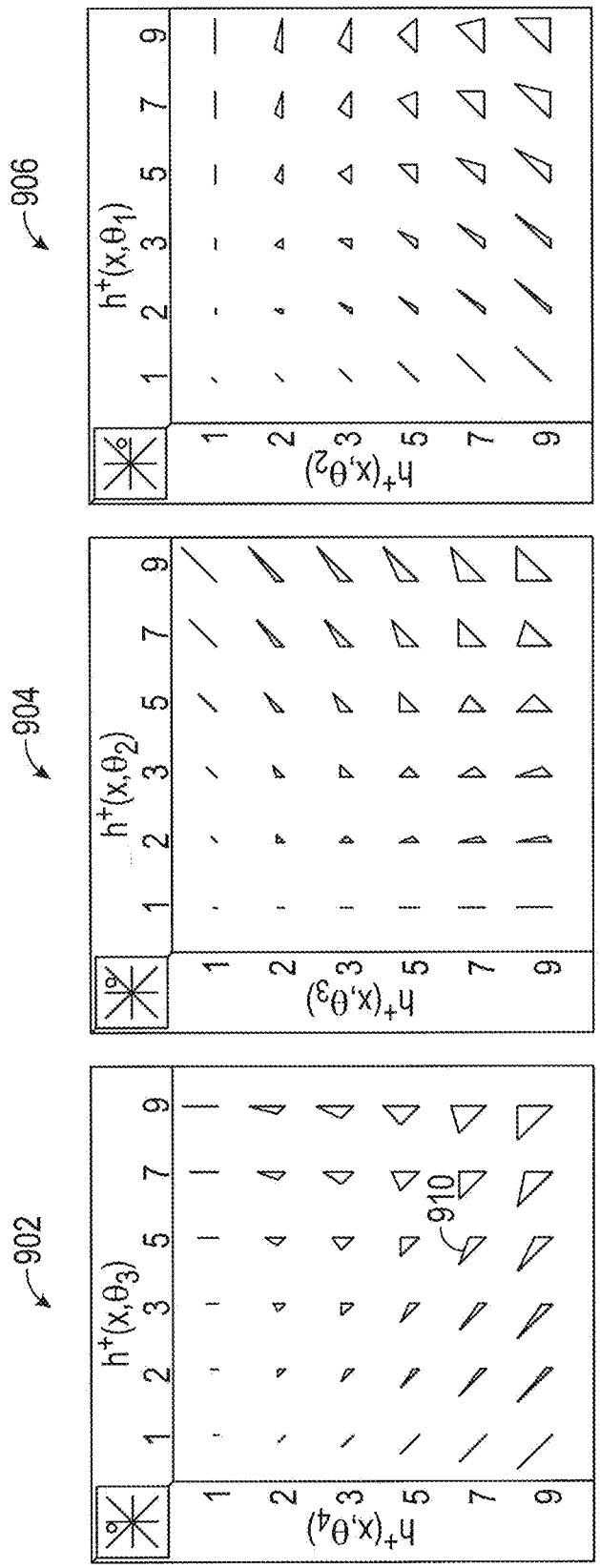
FIG. 9 illustrates examples of pre-calculated triangular stencils that may be used to determine which pixel coordinates belong to an adaptive-shape neighborhood based on line-wise extents, in accordance with an embodiment of the disclosure.

FIG. 9 illustrates examples of such pre-calculated triangular stencils for selected pairs of adaptive-scale kernel supports, in accordance with an embodiment of the disclosure.

Specifically, three example sets 902, 904, and 906 of such triangular stencils corresponding to the pairs ($h^+(x,\theta_3)$, $h^+(x,$ $\theta_4$)), ($h^+(x,\theta_2)$, $h^+(x,\theta_3)$), and (($x,\theta_1$), ($x,\theta_2$)) are shown in FIG. 9 for the scale (length) set $h \in H = \{1, 2, 3, 5, 7, 9\}$. That is, example triangular stencil sets 902, 904, and 906 show triangle stencils for possible pairs of adaptive-scale kernels in directions $\theta_3$ and $\theta_4$, for possible pairs of adaptive-scale kernels in directions $\theta_2$ and $\theta_3$, and for possible pairs of adaptive-scale kernels in directions $\theta_1$ and $\theta_2$, respectively, where each adaptive-scale kernel can have a length $h \in H = \{1, 2, 3, 5, 7, 9\}$. To illustrate the use of such pre-calculated triangular stencils, suppose that the determined line-wise extent for direction $\theta_3$ is 5 and the determined line-wise extent for direction $\theta_4$ is 7, for example. Then a pre-calculated triangular stencil 910 can be selected as the triangle that forms a part of the polygonal hull.

Such pre-calculated triangular stencils may be stored, indexed, and/or encoded using an appropriate data structure as desired for various embodiments. In one embodiment, for example, each triangular stencil may be encoded efficiently as an array of numbers indicating how many pixels (e.g., pixel coordinates) belong to the stencil and where they are located with respect to the center of the adaptive-shape neighborhood (e.g., how far in memory are those pixel coordinates). Thus, by using pre-calculated triangular stencils as discussed above for various embodiments, an adaptive-shape neighborhood may be provided efficiently based on the set of line-wise extents determined for each reference image pixel coordinate.

Therefore, at block 210 of process 200, adaptive-shape neighborhoods for all or some pixel coordinates of reference image 204 may be determined according to any of the various techniques discussed above with reference to FIGS. 3A-9. As illustrated above, such adaptive-shape neighborhoods adapt their shape (e.g., extent) in response to structural information (e.g., object contours, edges, or other structural details or change points), and thus reveal fine structural details and elements around a corresponding reference image pixel coordinate.

For example, in some embodiments, an adaptive-shape neighborhood (e.g., adaptive-shape neighborhood 304A) may be determined such that it extends anisotropically in a plurality of directions from a corresponding reference image pixel coordinate as the center to include those reference image pixels within the shape-adaptive neighborhood that meet a given regularity (e.g., smoothness) condition as shown in FIG. 3A. In some embodiments, an adaptive-shape neighborhood may be determined as a combination of adaptive-scale directional windows (e.g., adaptive-scale directional windows 306(1)-306(16)) as shown in FIGS. 3C and 4.

In some embodiments, adaptive-shape neighborhoods may be determined efficiently by using one-dimensional line-wise kernels for a predetermine set of directions. Determining an adaptive-shape neighborhood (e.g., adaptive-shape neighborhoods 502 and 602(1)-602(22)) according to such embodiments may include determining line-wise extents (e.g., lengths of line-wise adaptive-scale kernel supports) for a set of directions from a corresponding reference image pixel location as the center as shown in FIGS. 5 and 6. For example, each line-wise extent may be determined from the length or scale of a support that best approximates the corresponding reference image pixel among a set of varying-scale kernel supports. As a more specific example according to some embodiments, the length or scale of a line-wise LPA kernel that provides the best approximate among a set of line-wise LPA kernels may be selected as the line-wise extent, using a statistical method such as the ICI method, as discussed above with reference to FIGS. 7 and 8. A polygonal hull of the determined line-wise extents for each reference image pixel coordinate, which represents an adaptive-shape neighborhood associated with the pixel coordinate, may be obtained efficiently using pre-calculated triangles as discussed above with reference to FIG. 9, for example.

Turning now to block 212 of FIG. 2, the adaptive-shape neighborhoods determined based on reference image 204 at block 210 are applied to the resized target image 202 to determine a local estimate for a super-resolved version of target image 202 within each adaptive-shape neighborhood. Since the adaptive-shape neighborhoods may be determined for all or some plurality of reference image pixel coordinates, and since each reference image pixel coordinate may map also to a corresponding target image pixel that depicts a substantially same location in the scene as the reference image pixel for some embodiments (as discussed above in connection with block 208), the adaptive-shape neighborhoods determined based on reference image 204 can be used (e.g., applied) with respect to the resized target image 202 to determine local estimates based on the resized target image 202.

In other words, the adaptive-shape neighborhoods are determined based on pixels of reference image 204, while the local estimates for the adaptive-shape neighborhoods are determined based on corresponding target image pixels within the respective adaptive-shape neighborhoods as applied to the resized target image 202, by the correspondence of pixel coordinates in some embodiments or by other relationships that can identify corresponding reference and target image pixels that depict a substantially same location of the scene. In this way, the structural information (e.g., object contours, edges, or other structural details) from reference image 204 that is captured by the adaptive-shape neighborhoods can be applied to the resized target image 202 to improve the resolution, definition, and/or SNR of target image 202.

The local estimate for each the adaptive-shape neighborhood (as applied to the resized target image 202) may represent an estimate of super-resolved target image pixels within (e.g., belonging to) the adaptive-shape neighborhood, and may be determined in various ways according to embodiments of the disclosure. For example, in some embodiments, the local estimate may be determined as an average (e.g., a simple average, a weighted average, or by other averaging methods) of target image pixels within the adaptive-shape neighborhood (e.g., an average of the pixel values of those target image pixels). In other examples according to some embodiments, the local estimate may be determined by filtering (e.g., normalizing) the target image pixels within the adaptive-shape neighborhood. In other words, the local estimates in these embodiments may be filtered versions (e.g., normalized versions) of the target image pixels within the adaptive-shape neighborhood.

The filtering operations or filters that may be used in these embodiments include, for example, filtering using a shape-adaptive discrete cosine transform (SA-DCT) or other shape-adaptive harmonic transforms, filtering using adaptive transforms learned from mutual nonlocal similarity within various adaptive-shape neighborhoods, filters based on sparsity principles, and filters based on range and domain vicinity with vicinity weights given by the adaptive-shape neighborhoods (e.g., including a bilateral filter or nonlocal means filter).

Figure 10:
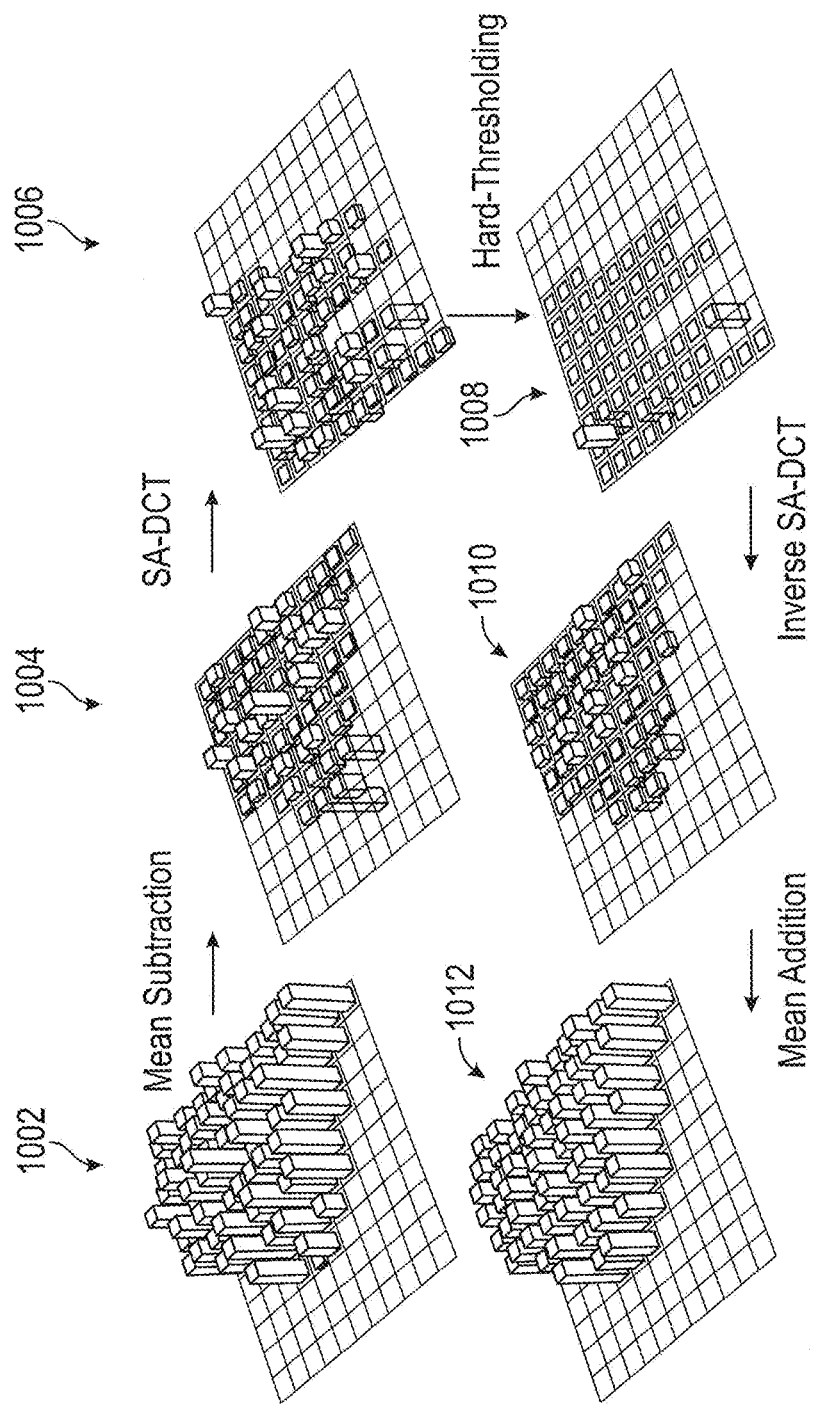
FIG. 10 illustrates how target image pixels within an adaptive-shape neighborhood may be filtered using a shape-adaptive discrete cosine transform to obtain a local estimate, in accordance with an embodiment of the disclosure.

As a non-limiting example of a filtering operation to determine the local estimate, FIG. 10 illustrates how target image pixels 1002 within an adaptive-shape neighborhood may be filtered using a SA-DCT (e.g., by thresholding in the SA-DCT domain) to obtain filtered target image pixels 1012 as the local estimate, in accordance with an embodiment of the disclosure. In FIG. 10, the height of the bars represents the pixel values for the target image pixels within the adaptive-shape neighborhood. According to the illustrated example, target image pixels 1002 within an adaptive-shape neighborhood may first be subtracted of its mean value to obtain mean-subtracted target image pixels 1004. This may be beneficial to reduce the "mean weighting effect," but may be omitted in other embodiments. A SA-DCT may be performed on mean-subtracted target image pixels 1004 (or on target image pixels 1002 if the mean subtraction is omitted) to obtain SA-DCT coefficients 1006 (coefficients in SA-DCT domain) that correspond to mean-subtracted target image pixels 1004 (or target image pixels 1002 if the mean subtracting operation is omitted).

The SA-DCT may be performed by a cascaded application of one-dimensional varying-length DCT first on the columns and then on the rows, or first on the rows and then on the columns, of target image pixels 1004 (or of target image pixels 1002 if the mean subtraction is omitted), or by other suitable application of a SA-DCT. In some embodiments, coefficients obtained after first one-dimensional transform may be aligned to improve their vertical or horizontal correlation before applying the second one-dimension transform.

Additionally in some embodiments, target image pixels 1004 (or target image pixels 1002) may be transformed first along its longest orientation to improve efficiency. In case adaptive-shape neighborhoods are determined using line-wise extents, the longest orientation of the adaptive-shape neighborhood can be easily determined using the determined line-wise extents. For example, if the line-wise extents (also referred to as adaptive-scales as discussed above) are determined for eight directions, the longest orientation of the adaptive-shape neighborhood may be determined using the four line-wise extents in the vertical and the horizontal directions based on the inequality: $h^+(x,\theta_1)+(x,\theta_5)>h^+(x,\theta_3)+h^+(x,\theta_7)$. If this inequality is satisfied, then the adaptive-shape neighborhood may be considered to be horizontally oriented and the SA-DCT may be performed first on rows and then on columns Otherwise, the SA-DCT may be performed first on columns and then on rows.

After SA-DCT coefficients 1006 are obtained by performing a SA-DCT, SA-DCT coefficients 1006 may be shrunk (e.g., by hard-thresholding or soft-thresholding) or otherwise modified to generate shrunk coefficients 1008. As shown for example in FIG. 10, many of SA-DCT coefficients 1006 may be eliminated by the shrinking, thereby normalizing, regularizing, or otherwise filtering the corresponding target image pixels in the spatial domain. For example, performing hard-thresholding on SA-DCT coefficients 1006 modifies SA-DCT coefficients to have zero or other small value if they do not meet a threshold value, thereby generating shrunk coefficients 1008.

Inverse of the SA-DCT may then be performed on shrunk coefficients 1008 to obtain filtered mean-subtracted image pixels 1010 in the spatial domain, and the mean value subtracted from target image pixel 1002 may be added back to obtain filtered image pixels 1012. Filtered image pixels 1012 are thus filtered (e.g., normalized, regularized) versions of target image pixels 1002 in the adaptive-shape neighborhood, and may be determined as the local estimate for the adaptive-shape neighborhood. As may be appreciated, if the mean subtraction step was omitted, the mean value need not be added back and the image pixels obtain after the inverse SA-DCT may be determined as the local estimate.

Therefore, after block 212 of process 200, a local estimate may be determined for each adaptive-shape neighborhood based on the target image pixels within the adaptive-shape neighborhood. Each local estimate may be a normalized, regularized, or otherwise filtered version of the target image pixels within the respective adaptive-shape neighborhood, and may be used as an estimate of a super-resolved version of target image 202 with respect to the area associated with the respective adaptive-shape neighborhood.

At block 214, the local estimates are aggregated or otherwise combined to provide a global estimate that represents a super-resolved version of the entire target image 202 or a selected portion or portions of target image 202. For example, if the adaptive-shape neighborhoods are determined for all pixel coordinates or otherwise sufficient number of pixel coordinates associated with reference image 204 and the resized target image 202, the local estimates determined for these adaptive-shape neighborhoods can be aggregated to obtain a global estimate that represents a super-resolved version of the entire target image 202. More generally, for example, local estimates of adaptive-shape neighborhoods determined for a sufficient number of pixel coordinates associated with any selected portion or portions of reference image 204 and the resized target image 202 may be used to construct a global estimate for a super-resolved version of a corresponding portion or portions of target image 202. It is contemplated that manual or automatic selection of a portion or portions of target image 202 to be super-resolved (e.g., areas of interest, such as areas with detailed structural information) may be provided for some embodiments, which may permit process 200 to be performed more efficiently since the adaptive-shape neighborhoods and their local estimates need to be determined for only the corresponding portions in reference image 204 and the resized target image 202, for example.

As discussed above, adaptive-shape neighborhoods associated with different pixel coordinates, such as those pixel coordinates that are close to one another, may often overlap. In this regard, the different local estimates that overlap may represent an overcomplete estimate of a super-resolved version of target image 202 for the overlapping portion. Thus, in various embodiments, the aggregating of the local estimates include averaging the local estimates. In general, the local estimates aggregated in this way produce a better estimate than each of the local estimates, according to the bias-variance trade-off principle.

In some embodiments, the local estimates may be weight-averaged. In further embodiments, the local estimates may be weight-averaged using adaptive weights that are based on the local estimates' statistics. As one specific example according to some embodiments, the adaptive weights may be determined as the inverse of the number of pixels belonging to the corresponding adaptive-shape neighborhoods. Thus, in this example, the larger the area to which an adaptive-shape neighborhood extends, the smaller the contribution of its local estimate becomes. In this regard, using the inverse of the number of pixels within the adaptive-shape neighborhood advantageously addresses situations in which a local estimate for a larger adaptive-shape neighborhoods "submerge" (e.g., dilute) the finer details restored by a local estimate for a smaller adaptive-shape neighborhood in areas where adaptive-shape neighborhoods of different sizes overlap (e.g., in images areas along edges or transition). In another example according to some embodiments, the adaptive weights may be inversely proportional to the average sample variance of the local estimate for the corresponding adaptive-shape neighborhood. In another example according to some embodiments, the adaptive weights may be responsive to both the size (e.g., number of pixels) and the average variance associated with the corresponding adaptive-shape neighborhood, such as for example being inversely proportional to both the size and the average sample variance.

Therefore, after block 214, a global estimate is obtained which may represent a super-resolved version (e.g., having an improved resolution, definition, and/or SNR) of the entire target image 202 (or a portion or portions of target image 202 if desired), since the local estimates are determined based on the pixels of the resized target image 202 with respect to respective adaptive-shape neighborhoods that are adapted to reveal and capture structural information (e.g., object contours, edges, or other structural details) in reference image 204 having a higher resolution, definition, and/or SNR than target image 202.

At block 216, the global estimate, which may represent a super-resolved version of target image 202, is compared with target image 202 to adjust the global estimate. For example, in various embodiments, differences between the global estimate and target image 202 may be evaluated and re-injected back into the global estimate to constrain the global estimate to target image 202 (e.g., ensure that the pixel value of each pixel in target image 202 are substantially preserved in the aggregate pixel value of corresponding group of pixels in the global estimate). This may be referred to herein as "back-projection."

To illustrate with an example, suppose the global estimate is a scaled and super-resolved version that has 2× (two-times) the original resolution (i.e., 4× the number of pixels) of target image 202. Then, one pixel in target image 202 is super-resolved to four pixels in the global estimate, and the four global estimate pixels may have four pixel values that are different from one another and/or from the one original target image pixel since they are super-resolved. Back-projection ensures that the aggregate (e.g., averaged or interpolated) pixel value of the four pixels in the global estimate corresponds to (e.g., substantially preserves) the pixel value of the one original target pixel. Thus, back-projection may advantageously preserve the overall radiometric observations or readings, such as radiometric temperature information in infrared images or distance/depth information in ToF or LIDAR images, represented by the pixel values of the original target image even when the original target image pixels are each super-resolved to multiple pixels in the global estimate.

Back-projection at block 216, according to some embodiments, may include: downsizing (e.g., downscaling or downsampling, such as by bilinear scaling) the global estimate to match the image dimension of target image 202; determining the difference in pixels values of the target image 202 and the downsized global estimate; upsizing (e.g., upscaling or upsampling, such as by bilinear interpolation) the difference back to match the image dimension of the global estimate; and adjusting the global estimate by adding the upsized difference to the global estimate. In pseudo-code, this may be expressed as:

difference=target_image−downsize(global_estimate);

global_estimate=global_estimate+upsize(difference).

In some embodiments, block 216 may also include evaluating the global estimate to adjust image registration parameters. As discussed above for block 206, an image registration (image alignment) process may be performed in some embodiments to align target image 202 and reference image 204. As may be appreciated, since process 200 assumes some correspondence of pixel coordinates between the resized target image 202 and reference image 204 for operations such as determining local estimates and back-projection, residual image registration errors may affect the quality of the global estimate or the back-projected global estimate. For example, the inventors have found through experiments carried out in connection with the disclosure that minor registration errors may create some minor "false edges" in the global estimate.

Thus, in some embodiments, the global estimate or the back-projected global estimate may be analyzed to detect such minor false edges. Based on the analysis and detection, for example if the occurrence of minor false edges exceeds a predetermined threshold, one or more parameters for the image registration process (e.g., parameters for feature or intensity detection sensitivity, selection of transforms) may be adjusted. In some embodiments, the adjusting of the image registration parameters may involve repeating, one or more times, process 200 from the image registration process at block 206 with the adjusted image registration parameters (e.g., repeating relevant parts of blocks 206-216) and re-evaluating the global estimate (or the back-projected global estimate) for minor false edges. In this way, for example, multiple candidates for image registration parameters may be obtained, and the candidate that yields the lowest edge energy (e.g., measured by some norm of the gradient of the global estimate) may be searched and chosen along with the resulting global estimate to obtain a global estimate that is not undesirably affected by image registration errors. This search and selection process may be a form of a direct-search optimization problem, and thus may be solved by Nelder-Mead simplex algorithm or other suitable method, for example.

At block 218, sensitivity (e.g., a sensitivity parameter) for determining the adaptive-shape neighborhoods is increased. At block 220, if it is determined that another iteration of blocks 210 through 218 is to be performed to obtain an updated global estimate with finer details (i.e., yes for the test at block 220), process 200 flows back to block 210 to perform another iteration from block 210 with the increased sensitivity parameter and with the global estimate (or the back-projected global estimate) provided as a new target image for block 210. If not (i.e., no for the test at block 220), process 200 proceeds to block 222.

As discussed above for block 210 and with reference to FIG. 8, the extent (e.g., shape) of each adaptive-shape neighborhood from a given reference image pixel coordinate is determined based on the regularity (e.g., smoothness) of reference image pixels at and surrounding the given image pixel coordinate, and the regularity condition or criteria for determining whether or not those pixels are sufficiently regular may be adjusted for its sensitivity. As also discussed, if the sensitivity for determining the adaptive-shape neighborhoods is increased, the size of each adaptive-shape neighborhood may decrease or stay the same at most (does not increase), such that finer structural details in reference image 204 may be revealed by the smaller-size adaptive-shape neighborhoods.

Thus, according to some embodiments, sensitivity for determining the adaptive-shape neighborhoods is increased and the operations for the determination of the adaptive-shape neighborhoods through the determination of the global estimate (or the back-projected global estimate) are repeated on the global estimate (or the back-projected global estimate) to obtain an updated global estimate that may reveal finer structural details. For example, in embodiments in which line-wise extents that provide support for an adaptive-shape neighborhood are determined using LPA kernels and the ICI method, the threshold parameter $\Gamma$ may be decreased to increase the sensitivity for determining adaptive-shape neighborhoods, as discussed above with reference to FIG. 8. The threshold parameter $\Gamma$ may be decreased exponentially in one embodiment.

The test at block 220 to determine whether to another iteration is to be performed may include, in some embodiments, determining whether the increased sensitivity has reached a predetermined threshold or not (e.g., whether the decreased threshold parameter $\Gamma$ is still above a predetermined threshold, such as $\Gamma>0$). In some embodiments, the test at block 220 may include determining whether blocks 210 through 218 have been repeated for a sufficient number of iterations or not (e.g., whether the number of iterations has reached a predetermined maximum number of iterations). In some embodiments, both the test for the sensitivity and the number of iterations may be included in the test at block 220.

Figure 11:
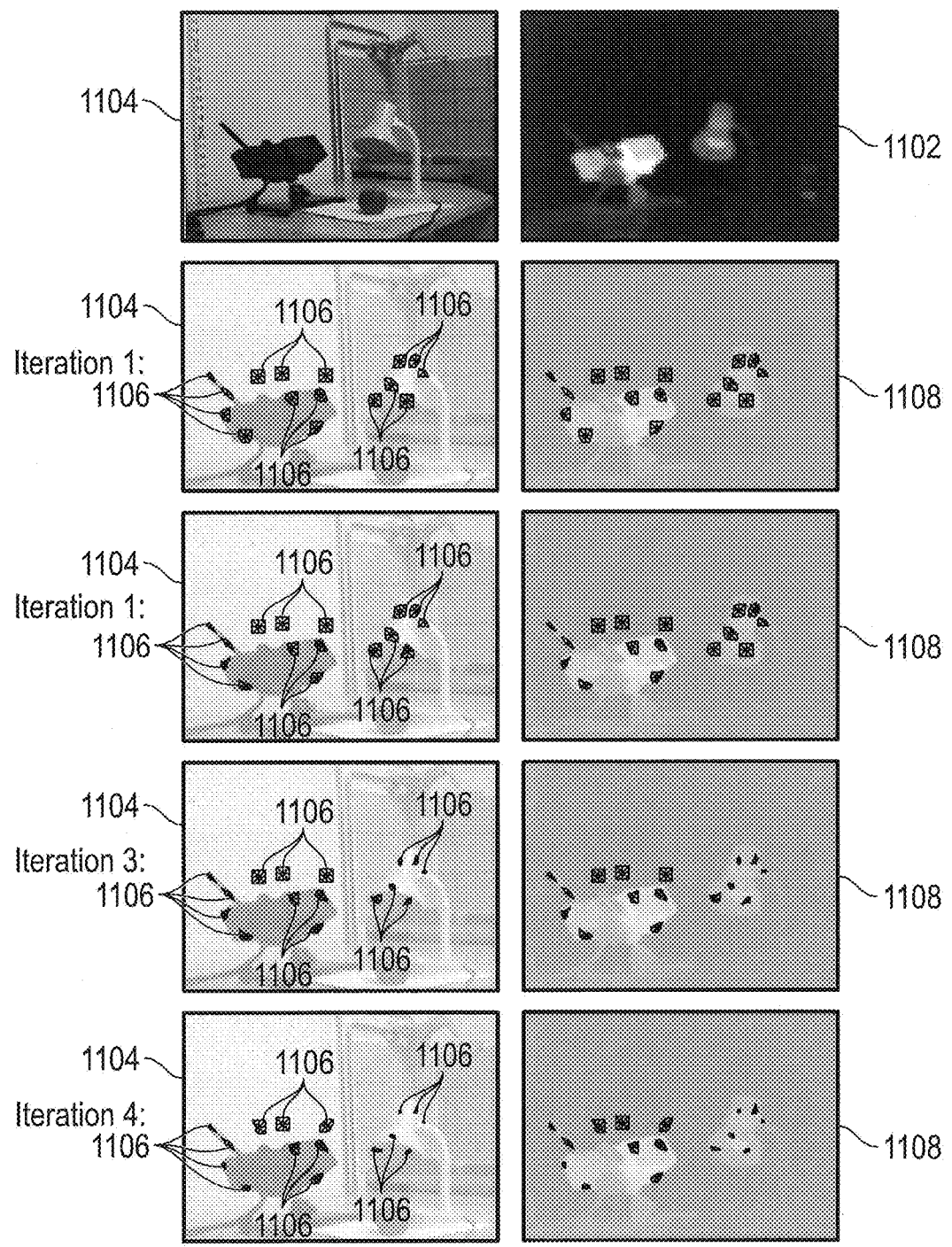
FIG. 11 illustrates an example progression of adaptive-shape neighborhoods and a global estimate as part of the process of FIG. 2 is repeated with increasing sensitivity for determining adaptive-shape neighborhoods, in accordance with an embodiment of the disclosure.

Referring also to FIG. 11, an example progression of the determined adaptive-shape neighborhoods and the global estimate is illustrated as blocks 210 through 218 are repeated for multiple iterations with increased sensitivity, in accordance with an embodiment of the disclosure. The example progression illustrated in FIG. 11 starts with a reference image 1104 and a resized target image 1102, shown at the top row. Reference image 1104 may be received at block 206, and adaptive-shape neighborhoods 1106 may be determined based on reference image 1104 with finer granularity by repetitions of block 210 with increasing sensitivity (e.g., decreasing values for threshold parameter $\Gamma$). Resized target image 1102 may be based on a target image received at block 206 and resized to a desired scale at block 208, and a global estimate 1108 may be updated by repetitions of blocks 212 and 214 (and also block 216 for some embodiments) to provide a super-resolved version of resized target image 1102 with increasing structural details as adaptive-shape neighborhoods 1106 are determined with finer granularity. Specifically, the example of FIG. 11 shows adaptive-shape neighborhoods 1106 and global estimate 1108 obtained for four iterations of blocks 210 through 218, during which at least some adaptive-shape neighborhoods 1106 become smaller in size to reveal finer structural details and global estimate 1108 is correspondingly updated to show sharper edges and more structural details.

It should be noted that reference image 1104 and global estimate 1108 are shown faded in FIG. 11 for iterations 1 through 4 for purposes of clearly indicating adaptive-shape neighborhoods. That is, operations of blocks 210 through 218 do not actually or necessarily produce such faded reference image 1104 and global estimate 1108. Note also that adaptive-shape neighborhoods are indicated on global estimate 1108 to illustrate the application of the determined adaptive-shape neighborhoods at corresponding pixel locations of the resized target image 1102 and global estimate 1108 as discussed above for block 212; it should be appreciated that adaptive-shape neighborhoods 1106 are determined based on reference image 1104, as discussed above for block 210.

After blocks 210 through 220 have been repeated for a desired number of iterations to obtain an updated global estimate with finer structural details, process 200 flows to block 222 to check whether the global estimate representing a super-resolved version of target image 202 has a desired image dimension (e.g., size) or not. If not, process flows back to block 208 to resize (e.g., upscale or upsample) the global estimate to a larger dimension and repeat blocks 208 through 222 with the resized global estimate as a new resized target image. If assuming, for example, the global estimate was obtained with 2× the size (e.g., image dimension) of the original target image 202 with one run of blocks 208 through 222 but super-resolution to 8× the original target image 202 size is desired, then the test at block 222 would cause process 200 to repeat blocks 208 through 220 once to obtain a global estimate with 4× the original target image 202 size and twice to obtain a global estimate with 8× the original target image 202 size.

If the test at block 222 is satisfied, a global estimate is obtained that corresponds to (and thus can be used as) a super-resolved version of the original target image 202 at a desired image dimension. Thus, after block 222, a super-resolved version of a natively low resolution image (e.g., LWIR image, ToF image) is obtained, which may provide sharper, easier-to-interpret, more visually pleasing, and more content-rich images and videos for viewing by users when displayed, and improve the performance of various other video processing and analytics operations such as object detection, object identification, target tracking, segmentation, scene tracking, and other analytics operations when provided as an input to those operations.

Process 200 according to the illustrated embodiment of FIG. 2 includes blocks 224 and 226 to further enhance the super-resolved image. In particular, at block 224, the global estimate obtained after block 222 is sharpened based on edge information (e.g., location of edges, contours, and/or other structural details) extracted from reference image 204. Any suitable image sharpening filter may be applied for each of a plurality of pixel from the global estimate (e.g., from the entire global estimate or from one or more desired portions of the global estimate), where one or more parameters for the chosen sharpening filter may be adjusted based on the presence of edges, contours, and/or other structural details at and around the pixel as determined based on reference image 204. In one example according to some embodiments, a modified trilateral sharpening filter may be applied. Specifically, a weighted averaging over a 3×3 neighborhood of each pixel may be performed, where the weights are based on the edge information for the corresponding area as extracted from reference image 204.

In some embodiments, block 224 may include resizing the global estimate to a larger image dimension, in a similar manner as described for block 208. Thus, in these embodiments, imaging sharpening at block 224 is performed on the resized global estimate. Furthermore, according to some embodiments, more than one iteration of such resizing and sharpening of the global estimate may be performed at block 224 to achieve the desired resolution. For embodiments in which the resizing and sharpening of the global estimate is iterated more than once until the desired resolution is achieved, back-projection may be performed in between the iterations to preserve the overall radiometric observations or readings as described above for block 216.

At block 226, edge information extracted from reference image 204 is overlaid or otherwise combined with the global estimate (e.g., the sharpened global estimate in some embodiments). For example, edge information may be extracted from reference image 204 and added to or otherwise used to modify the global estimate (e.g., added to a luminance channel or otherwise used to modify pixel values) in accordance with various techniques disclosed in U.S.

patent application Ser. No. 14/922,076 entitled "Infrared Resolution and Contrast Enhancement with Fusion" and filed Oct. 23, 2015, U.S. Pat. No. 9,171,361 entitled "Infrared Resolution and Contrast Enhancement with Fusion" and issued Oct. 27, 2015, U.S. Pat. No. 8,565,547 entitled "Infrared Resolution and Contrast Enhancement with Fusion" and issued Oct. 22, 2013, and U.S. Pat. No. 8,520,970 entitled "Infrared Resolution and Contrast Enhancement with Fusion" and issued Aug. 27, 2013, all of which are incorporated herein by reference in their entirety. Blocks 224 and/or 226 may be omitted in other embodiments, however.

Thus, after block 222, a global estimate is obtained that corresponds to a super-resolved version of the original target image 202 at a desired image dimension, after block 224, the global estimate is further sharpened based on the edge information extracted from reference image 204, and after block 226, the global estimate is further enhanced with the edge information overlaid onto the global estimate. Note, however, that blocks 224 and/or 226 may be omitted in other embodiments.

Figure 12A:
FIGS. 12A-12D illustrate example input and output images of the process of FIG. 2, in accordance with an embodiment of the disclosure.
Figure 12B:
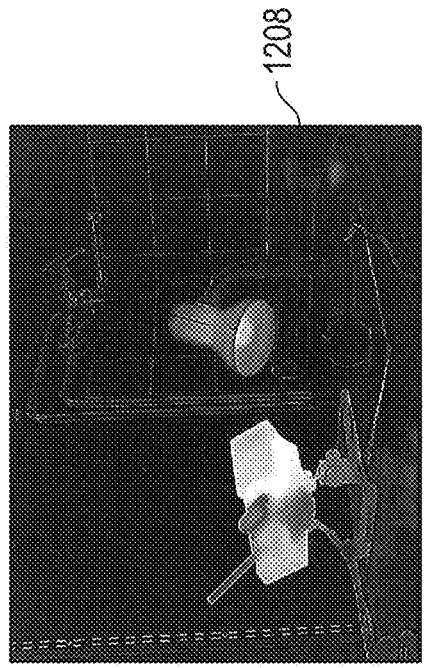
Figure 12C:
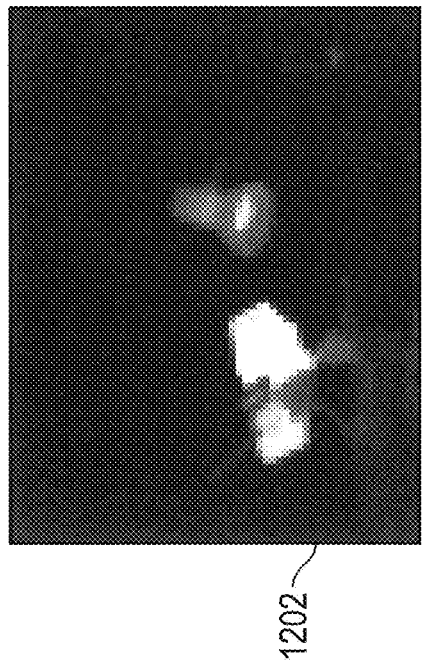
Figure 12D:
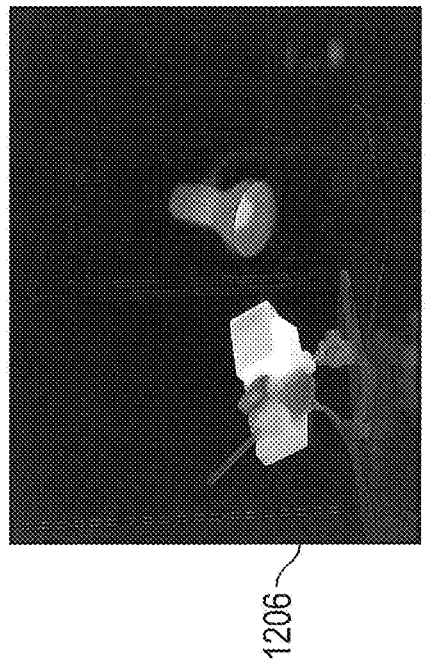

Examples of an original target image and the obtained global estimate at these various stages of processing are illustrated in FIGS. 12A-D for comparison, in accordance with an embodiment of the disclosure. In particular, FIG. 12A shows an example of an original target image 1202 (e.g., target image 202) to be super-resolved, FIG. 12B shows a global estimate 1204 corresponding to a super-resolved version of the original target image obtained after block 222 (e.g., after one or more iterations of blocks 210 through 220 and blocks 208 through 222), FIG. 12C shows a sharpened global estimate 1206 obtained after block 224, and FIG. 12D shows a sharpened global estimate with edge information overlaid 1208 after block 226. As the examples in FIGS. 12A-B show, global estimate 1204 that corresponds to a super-resolved version of original target image 1202 shows objects with higher resolution, higher definition, and more structural details than original target image 1202 that shows the objects in coarse pixels and with fuzzy outlines and edges. Sharpened global estimate 1206 shows even sharper outlines, edges, and contours of the object than global estimate 1204. Sharpened and edge-overlaid global estimate 1208 shows outlines, edges, and contours that were not visible in original target image 1202 for an improved interpretation and understanding of the scene and the objects when viewed by a user.

Therefore, the methods and systems disclosed herein according to various embodiments may be utilized to enhance the resolution, definition, and/or SNR of target images to provide sharper, easier-to-interpret, more visually pleasing, and more content-rich images and videos for viewing and for further image processing. Such beneficial enhancement of the image resolution is obtained using adaptive-shape neighborhoods that adapt their shapes (e.g., extents) to structural information captured in a higher resolution "pilot" or "reference" image depicting the same scene as the target image, as discussed above for various embodiments. Such adaptive-shape neighborhoods may be determined based on a reference image to reveal and capture structural details contained in the reference image, in an efficient and effective manner according to the techniques disclosed herein in connection with various embodiments. The adaptive-shape neighborhoods are applied to an upsized target image to obtain local estimates for a super-resolved image with respect to the adaptive-shape neighborhoods, and the local estimates are aggregated to provide a global estimate that corresponds to a super-resolved version of the target image (e.g., the entire target image or selected areas of the target image). The global estimate can be updated for multiple times with increasingly finer structural information using adaptive-shape neighborhoods that are increasingly sensitive to the regularity (e.g., smoothness) of the reference image pixels that fall within it and thus may be smaller in size to adapt to finer structural details. The global estimate can be further enhanced as desired to sharpen and/or to add edges, contours, and/or outlines in the global estimate, based on information extracted from the reference image.

Although the various embodiments above are illustrated with two dimensional (2-D) target and reference images as examples, the techniques described above for various embodiments can be applied to higher dimensional target and reference images (e.g., 3-D images, or any n-dimensional images) as discussed above with reference to FIGS. 3D, 3E, and 6B. In this regard, relevant operations of method 200 of FIG. 2 may be performed with respect to three axes (x, y, and z axes) or any n-dimensional coordinate system to enhance three or higher dimensional target images. In an example 3-D application, adaptive-shape neighborhoods may be determined so that they extend from each reference 3-D volumetric image voxel in x, y, and z axes to form a volume (e.g., a polyhedral hull in embodiments that approximate the adaptive-shape neighborhoods using line-wise extents as discussed above but in the three axes) that includes those voxels that meet a given regularity condition, and the adaptive-shape neighborhoods determined from the reference 3-D volumetric image may be applied to corresponding voxels of the resized target 3-D volumetric image to obtain volumetric local estimates that are aggregated to provide a global estimate for the super-resolved target 3-D volumetric image.

For example, in medical imaging applications capturing 3-D volumetric images of a patient's body, a lower resolution volumetric image (e.g., captured by a PET scanner) may be enhanced using a higher resolution volumetric image (e.g., captured by a CT scanner) as a reference image. In yet another example, such 3-D volumetric images collected over time may collectively provide 4-D images with different imaging and time resolutions, which can be enhanced according to various embodiments of the disclosure. Cross-enhancement is also contemplated where images can be both target and reference images with respect to different dimensions. For example, a 4-D image that has a lower 3-D imaging resolution but a higher time resolution (e.g., captured with shorter time intervals) may be used as a reference image with respect to the time resolution, while at the same time be a target image with respect to the 3-D imaging resolution.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. A method comprising performing, by a system having a memory and a processing component, operations of:
   receiving a reference image of a scene, the reference image comprising reference image pixels identified by pixel coordinates;
   receiving a target image of the scene, the target image having a lower resolution than the reference image;
   resizing the target image to a larger image size, the resized target image comprising target image pixels identified by the pixel coordinates of the corresponding reference image pixels;
   for each reference image pixel in a plurality of reference image pixels, determining an adaptive-shape neighborhood for the reference image pixel coordinate, wherein the adaptive-shape neighborhood has a shape depending on the reference image pixel values and extends from the reference image pixel coordinate such that those reference image pixels that are within the adaptive-shape neighborhood meet a predetermined condition relevant to the reference image pixel values;
   determining, for each adaptive-shape neighborhood, a local estimate of a super-resolved version of the target image based on those target image pixels that are within the adaptive-shape neighborhood, the super-resolved version having an improved resolution relative to the target image received in said receiving; and
   aggregating the local estimates associated with the adaptive-shape neighborhoods to provide a global estimate that corresponds to the super-resolved version of the target image.

2. The method of claim 1, wherein:
   the reference image is a visible light image captured by a visible light imaging sensor; and
   the target image is an infrared (IR) image captured by an IR imaging sensor;
   wherein at least two adaptive-shape neighborhoods overlap at an overlapping portion, and the aggregating of the local estimates comprises combining the local estimates of the overlapping adaptive-shape neighborhoods to obtain the global shape estimate for the overlapping portion.

3. The method of claim 1, wherein:
   the reference image is captured by a computed tomography (CT) scanner or magnetic resonance imaging (MM) device;
   the target image is captured by a positron emission tomography (PET) scanner, single-photon emission computed tomography (SPECT) scanner, or ultrasound imaging device; and
   the processing component comprises one or more of: a processor, a microprocessor, a single-core processor, a multi-core processor, a microcontroller, a programmable logic device (PLD), a field programmable gate array (FPGA), a digital signal processing (DSP) device.

4. The method of claim 1, wherein the reference image and the target image are three-dimensional (3-D) volumetric or point-cloud images, and wherein the determining of each adaptive-shape neighborhood comprises determining adaptive-size cubes for 8 octants from each pixel coordinate.

5. The method of claim 1, wherein each adaptive-shape neighborhood extends anisotropically in a plurality of directions, wherein the determining of each adaptive-shape neighborhood comprises determining line-wise extents for a plurality of directions from each pixel coordinate, and wherein each adaptive-shape neighborhood is a polygonal hull of the determined line-wise extents for each pixel coordinate.

6. The method of claim 1, wherein the determining of each adaptive-shape neighborhood comprises determining line-wise extents for a plurality of directions from each pixel coordinate, and wherein determining of the line-wise extent for each direction comprises selecting, according to a statistical method, a local polynomial approximation (LPA) kernel from a set of LPA kernels with different lengths, the length of the selected LPA kernel being determined as the line-wise extent for the each direction.

7. The method of claim 6, wherein each selected LPA kernel is the lengthiest LPA kernel among the set of LPA kernels that provides an acceptable approximation according to the statistical method when the selected LPA kernel is convolved with those reference image pixels along the corresponding direction and length, or wherein the statistical method for selecting LPA kernels comprises an intersection of confidence intervals (ICI) method.

8. The method of claim 1, wherein the determining of the local estimate for each adaptive-shape neighborhood comprises averaging those target image pixels that are within each adaptive-shape neighborhood, or wherein the determining of the local estimate for each adaptive-shape neighborhood comprises filtering those target image pixels that are within each adaptive-shape neighborhood by:
   performing a shape-adaptive transform on those target image pixels within each adaptive-shape neighborhood to obtain coefficients corresponding to those target image pixels in the domain of the shape-adaptive transform, wherein the shape-adaptive transform comprises a shape-adaptive discrete cosine transform (SA-DCT); and
   modifying the coefficients in the domain of the shape-adaptive transform.

9. The method of claim 1, wherein the aggregating comprises averaging the local pixel estimates according to weights associated with the respective local estimates, and wherein the weights are inversely proportional to the number of pixel coordinates belonging to the corresponding adaptive-shape neighborhoods.

10. The method of claim 1, further comprising repeating, with the global estimate used as the target image, the determining of the adaptive-shape neighborhoods, the determining of the local estimates, and the aggregating of the local estimates, and wherein the repeating is performed with increased sensitivity for the predetermined condition for determining the adaptive-shape neighborhoods, such that at least some of the adaptive-shape neighborhoods become smaller to adapt to finer details captured in the reference image than those prior to the repeating.

11. The method of claim 1, further comprising:
   comparing the global estimate with the target image;
   adjusting the global estimate based on the comparing to remove or reduce differences in aggregate pixel values between the global estimate and the target image;

extracting edge information from the reference image; and either sharpening the global estimate based on the extracted edge information; or overlaying the edge information onto the global estimate.

12. A system comprising:
a video interface configured to receive image data or signals;
a processing component in communication with the video interface and configured to:
receive a reference image of a scene, the reference image comprising reference image pixels identified by pixel coordinates;
receive a target image of the scene, the target image having a lower resolution than the reference image;
resize the target image to a larger image size, the resized target image comprising target image pixels identified by the pixel coordinates of the corresponding reference image pixels;
for each reference image pixel in a plurality of reference image pixels, determine an adaptive-shape neighborhood for the reference image pixel coordinate, wherein the adaptive-shape neighborhood has a shape depending on the reference image pixel values and extends from the each pixel coordinate such that those reference image pixels that are within the adaptive-shape neighborhood meet a predetermined condition relevant to the reference image pixel values;
determine, for each adaptive-shape neighborhood, a local estimate of a super-resolved version of the target image based on those target image pixels that are within the adaptive-shape neighborhood, the super-resolved version having an improved resolution relative to the target image received in said receiving; and
aggregate the local estimates associated with the adaptive-shape neighborhoods to provide a global estimate that corresponds to the super-resolved version of the target image; and
a memory in communication with the processing component and configured to store the global estimate.

13. The system of claim 12, further comprising:
a first imaging sensor in communication with the video interface and configured to capture the reference image; and
a second imaging sensor in communication with the video interface and configured to capture the target image;
wherein the processing component is further configured to determine an overlapping portion of at least two overlapping adaptive-shape neighborhoods, and to aggregate the local estimates of the at least two overlapping adaptive-shape neighborhoods by at least combining the local estimates of the overlapping adaptive-shape neighborhoods to obtain the global shape estimate for the overlapping portion.

14. The system of claim 13, wherein:
the first imaging sensor comprises a visible light (VL) imaging sensor, a ultraviolet (UV) imaging sensor, a near-infrared (NIR) imaging sensor, computed tomography (CT) scanner or magnetic resonance imaging (MM) device; and
the second imaging sensor comprises an infrared (IR) imaging sensor, a time-of-flight (ToF) imaging sensor, a laser imaging detection and ranging (LIDAR) sensor, a millimeter wave (MMW) imaging sensor, a positron emission tomography (PET) scanner, single-photon emission computed tomography (SPECT) scanner, or ultrasound imaging device.

15. The system of claim 12, wherein the reference image and the target image are three-dimensional (3-D) volumetric or point-cloud images, and wherein the processing component is configured to determine each adaptive-shape neighborhood at least by determining adaptive-size cubes for 8 octants from each pixel coordinate; or
wherein each adaptive-shape neighborhood extends anisotropically in a plurality of directions.

16. The system of claim 12, wherein the processing component is configured to determine each adaptive-shape neighborhood at least by determining line-wise extents for a plurality of directions from each pixel coordinate, and wherein each adaptive-shape neighborhood is a polygonal hull of the determined line-wise extents for each pixel coordinate, or
wherein the determining of the line-wise extent for each direction comprises selecting, according to a statistical method, a local polynomial approximation (LPA) kernel from a set of LPA kernels with different lengths, the length of the selected LPA kernel being determined as the line-wise extent for the each direction, and wherein each selected LPA kernel is the lengthiest LPA kernel among the set of LPA kernels that provides an acceptable approximation according to the statistical method when the selected LPA kernel is convolved with those reference image pixels along the corresponding direction and length, and wherein the statistical method for selecting LPA kernels comprises an intersection of confidence intervals (ICI) method.

17. The system of claim 12, wherein the processing component is configured to determine the local estimate for each adaptive-shape neighborhood at least by averaging those target image pixels that are within each adaptive-shape neighborhood.

18. The system of claim 12, wherein the processing component is configured to determine the local estimate for each adaptive-shape neighborhood at least by filtering those target image pixels that are within each adaptive-shape neighborhood, and
wherein the filtering of the target image pixels comprises:
performing a shape-adaptive transform on those target image pixels within each adaptive-shape neighborhood to obtain coefficients corresponding to those target image pixels in the domain of the shape-adaptive transform, wherein the shape-adaptive transform comprises a shape-adaptive discrete cosine transform (SA-DCT); and
modifying the coefficients in the domain of the shape-adaptive transform.

19. The system of claim 12, wherein the processing component is configured to aggregate the local estimates at least by averaging the local pixel estimates according to weights associated with the respective local estimates, and wherein the weights are inversely proportional to the number of pixel coordinates belonging to the corresponding adaptive-shape neighborhoods; or
wherein the processing component is configured to repeat, with the global estimate used as the target image, the determining of the adaptive-shape neighborhoods, the determining of the local estimates, and the aggregating of the local estimates, wherein the processing component is configured to repeat the determining of the adaptive-shape neighborhoods, the determining of the local estimates, and the aggregating of the local estimates with increased sensitivity for the predetermined condition for determining the adaptive-shape neighborhoods, such that at least some of the adaptive-shape neighborhoods become smaller to adapt to finer details captured in the reference image than those prior to the repeating.

20. The system of claim 12, wherein the processing component is configured to:
compare the global estimate with the target image;
adjust the global estimate based on the comparison to remove or reduce differences in aggregate pixel values between the global estimate and the target image;
extract edge information from the reference image; and either
sharpen the global estimate based on the extracted edge information; or
overlay the edge information onto the global estimate.

* * * * *